(12) United States Patent
Hizume et al.

(10) Patent No.: US 8,842,173 B2
(45) Date of Patent: Sep. 23, 2014

(54) BIOLOGICAL IMAGE ACQUISITION DEVICE

(75) Inventors: Kentaro Hizume, Kyoto (JP); Ichiro Oda, Kyoto (JP); Atsushi Yajima, Kyoto (JP); Yoshio Tsunazawa, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 816 days.

(21) Appl. No.: 12/809,042

(22) PCT Filed: Dec. 25, 2008

(86) PCT No.: PCT/JP2008/073543
§ 371 (c)(1),
(2), (4) Date: Mar. 24, 2011

(87) PCT Pub. No.: WO2009/081969
PCT Pub. Date: Jul. 2, 2009

(65) Prior Publication Data
US 2011/0164124 A1 Jul. 7, 2011

(30) Foreign Application Priority Data
Dec. 26, 2007 (WO) .................. PCT/JP2007/074993

(51) Int. Cl.
*H04N 7/18* (2006.01)
*G01N 21/64* (2006.01)
*G06T 15/50* (2011.01)

(52) U.S. Cl.
CPC .................................. *G01N 21/6456* (2013.01)
USPC ........................................... 348/61; 345/426

(58) Field of Classification Search
USPC .......................................................... 348/61
See application file for complete search history.

(56) References Cited

U.S. PATENT DOCUMENTS 6,621,065 B1 * 9/2003 Fukumoto et al. ............ 250/216
6,922,246 B2 7/2005 Nilson et al.
(Continued)

FOREIGN PATENT DOCUMENTS

JP 3-111745 A 5/1991
JP 7-099005 A * 7/1995 ................ F21Q 3/00
(Continued)

OTHER PUBLICATIONS

International Search Report for the Application No. PCT/JP2008/073543 mailed Feb. 3, 2009.

*Primary Examiner* — Sath V Perungavoor
*Assistant Examiner* — Howard D Brown, Jr.
(74) *Attorney, Agent, or Firm* — Cheng Law Group, PLLC

(57) ABSTRACT

This object aims to disclose a biological multi-directional observation device with measures to avoid an illumination backlight problem taken. In a preferable embodiment of the multi-directional observation device, a two-dimensional detector (6) is arranged right above a transparent specimen support (2) and a main image forming lens (8) is arranged right under the two-dimensional detector (6). A fluorescence-side filter (10) which allows only a fluorescence component from a biological specimen (4) pass therethrough is arranged, if necessary, between the main image forming lens (8) and the biological specimen (4). Reflection mirrors (M1, M2) are arranged on the down side of the specimen support (2), wherein the reflection mirrors are optional systems for leading a light of an image of the rear side of the biological specimen (4) to the main image forming lens (8). A light source device is provided to irradiate light to biological specimen (4). A light source in the light source device is set at a position that is not in direct and indirect viewing fields (16, 18) of the two-dimensional detector, so that the backlight problem is avoided and a vivid biological multi-directional observation image by the two-dimensional observation image by the two-dimensional detector can be acquired.

17 Claims, 14 Drawing Sheets

(56) References Cited

U.S. PATENT DOCUMENTS

| | | | |
|---|---|---|---|
| 7,408,703 B2 * | 8/2008 | Matsuki et al. | 359/365 |
| 7,479,990 B2 * | 1/2009 | Imaizumi et al. | 348/223.1 |
| 7,528,398 B2 * | 5/2009 | Ikami | 250/522.1 |
| 8,164,622 B2 * | 4/2012 | Crandall | 348/79 |
| 8,345,941 B2 * | 1/2013 | Oda et al. | 382/128 |
| 2003/0214581 A1 | 11/2003 | Ikami | |
| 2004/0263643 A1 | 12/2004 | Imaizumi et al. | |
| 2005/0201614 A1 | 9/2005 | Rice et al. | |
| 2006/0238757 A1 * | 10/2006 | Silcott | 356/338 |
| 2007/0189763 A1 * | 8/2007 | Kojima et al. | 396/351 |
| 2011/0164124 A1 * | 7/2011 | Hizume et al. | 348/61 |
| 2013/0208241 A1 * | 8/2013 | Lawson et al. | 351/206 |
| 2014/0118353 A1 * | 5/2014 | Ha et al. | 345/426 |

FOREIGN PATENT DOCUMENTS

| | | | | |
|---|---|---|---|---|
| JP | 8-125835 A * | 5/1996 | | H04N 1/387 |
| JP | 10-124648 A | 5/1998 | | |
| JP | 2001-330915 A | 11/2001 | | |
| JP | 2003-287497 A | 10/2003 | | |
| JP | 2005-13611 A | 1/2005 | | |
| WO | WO-2007/094758 A2 | 8/2007 | | |
| WO | WO-2007/108070 A1 * | 9/2007 | | G06T 1/00 |

* cited by examiner

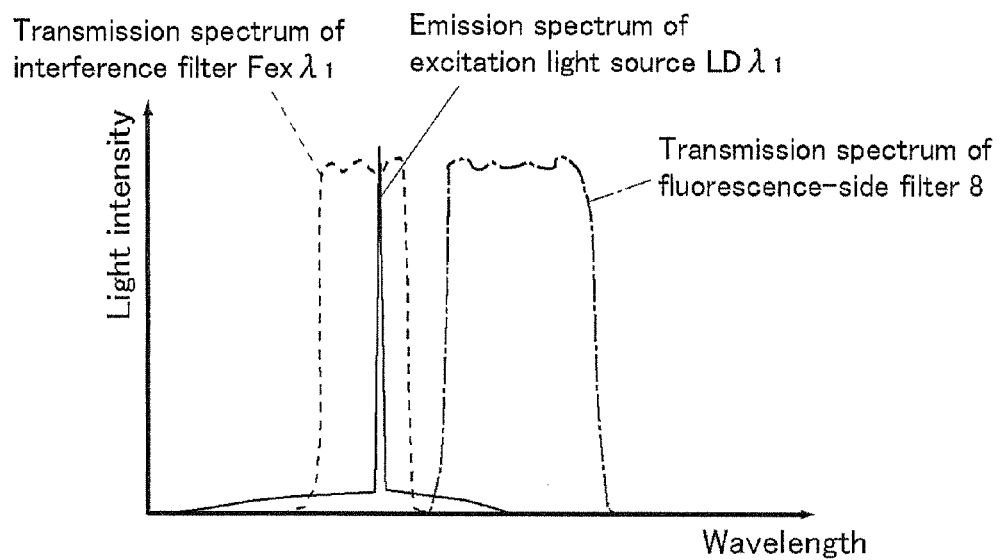

BIOLOGICAL IMAGE ACQUISITION DEVICE

BACKGROUND OF THE INVENTION

1. Field of the Invention

The present invention relates to an optical bioimaging technology for biological specimens such as small animals. More particularly, the present invention relates to a technique for avoiding the degradation of images of a living body simultaneously picked up by a multi-directional image acquisition device due to an illumination backlight problem.

2. Description of the Related Art

In medical and biological fields, imaging of the distribution of molecular species in a living body is an important research technique. Heretofore, cellular-level imaging of molecular species has been widely performed using a microscope and a molecular probe labeled with fluorochrome or a chemiluminescent molecular probe. On the other hand, there has been a demand for a device capable of observing the distribution of molecular species of interest in a living body not at the cellular level but at the level of organ or the entire animal body larger than cells. Such a device makes it possible to acquire images of a living body, such as a mouse, whose cancer cells are labeled with fluorescence probes every day or every week to monitor the growth of cancer cells of interest with the lapse of time. In a case where the growth of cancer cells in the body of an animal is observed by a conventional cellular-level observation device, it is necessary to kill the animal to stain a site to be observed or to attach a fluorescent substance to cancer cells. In this case, however, it is impossible to monitor the growth of cancer cells in one animal body over a long period of time. For this reason, there has been a demand for development of a device capable of observing molecular species in the body of a living small animal to obtain internal information of the small animal.

Near-infrared light relatively easily penetrates a living body. Therefore, light ranging from about 600 nm to 900 nm is used in devices for observing small animals. However, according to a conventional observation technique, a specimen is usually observed only from above and cannot be simultaneously observed from various directions. Therefore, there is a case where, for example, when a mouse is observed from a specific direction, cancer is not detected, but when the mouse is observed from a direction opposite to the specific direction, cancer is detected. When a mouse is observed using an unidirectional observation device, an operator has no choice to observe the mouse by a method approximate to multi-directional observation by picking up multi-directional images of the mouse rotated about its body axis by small increments. However, in this case, reproducible data cannot be obtained, and the mouse cannot be simultaneously observed from various directions. Particularly, in the case of observation of luminescence from a living body, the intensity of luminescence is very weak, and therefore, it is usually necessary to perform integrated exposure on a two-dimensional detector for several tens of seconds to a few minutes. On the other hand, the intensity of luminescence changes with time, and therefore, when image pickup is performed every time the observation direction is changed, image pickup conditions are different among image pickup directions and, thus, resulting images are useless. For this reason, it is preferred that two or more images of a living body picked up from two or more directions can be simultaneously and parallelly integrated on a detector for a long period of time. In the case of fluorescence observation, it is possible to perform fluorescence image measurement in a relatively short period of time. Still, it is absolutely necessary to simultaneously pick up information from various directions to speedily obtain accurate data.

As a method for acquiring multi-directional images, one for sequentially acquiring images observed from various angles using a rotating reflection mirror in a time-sharing manner is known (see Patent Document 1). According to this method, a specimen can be observed from various directions by rotating the mirror and by changing the position of the specimen itself by parallel displacement, and therefore, it is not necessary to rotate the specimen and a two-dimensional detector. However, the method disclosed in Patent Document 1 uses a rotating reflection mirror and therefore has the following drawbacks: a specimen is measured from various directions in a time-sharing manner, that is, multi-directional simultaneous measurement cannot be performed, and therefore, it takes a long time to complete measurement; images observed from different directions are picked up at different times and therefore lack in accuracy in the case of, for example, luminescence measurement because the intensity of luminescence changes with time; and a device using a rotating reflection mirror has a complicated structure.

Some image pickup optical systems not using a rotating reflection mirror are also known (see Patent Documents 2 to 9). Patent Documents 2 and 3 each describe the concepts of multi-directional observation and an image pickup optical system for multi-directional observation including a reflection mirror and a two-dimensional detector. The multi-directional observation devices described in Patent Documents 2 and 3 are merely target devices of the present invention, and there is no description about a backlight problem in Patent Documents 2 and 3. Patent Document 4 relates to a technique for "utilizing" light from the opposite side of a camera, and therefore has nothing in common with the present invention dealing with a technique for "avoiding" light from the opposite side of a camera. Patent Document 6 does not describe a technique for multi-directional observation of a specimen but describes a technique for picking up a panoramic (360°) image around a camera. Therefore, Patent Document 6 has no bearing on the present invention because the relationship between a specimen and a camera is the reverse of that in the present invention. Patent Documents 5, 7, and 8 do not describe even multi-directional observation. Patent Document 7 shows concentric arrangement of light sources in FIG. 1 by chance, but this arrangement is not intended to overcome a backlight problem and therefore gives no clue to the solution of problems to be solved by the present invention. Each of the Patent Documents 2 to 9 will be further described in detail as follows.

Patent Document 2 relates to an invention for photographing a three-dimensional image of an object. The only similarity between this invention and the present invention is the use of a polygonal mirror, but this invention is not intended to acquire biological information such as fluorescence images. Further, Patent Document 2 describes that the angle of the reflection mirror is made variable to increase the number of observation directions, but this means that observation is performed in a partial time-sharing manner, whereas the present invention is intended to perform simultaneous observation. Further, there is a description about the use of a light source, but this light source is arranged simply to illuminate a dark back side of a specimen. Therefore, Patent Document 2 does not, of course, describe a backlight problem caused by the light source for illuminating the back side of a specimen, and does not at all consider the possibility of direct entry of light from the light source into a camera. For this reason, the invention disclosed in Patent Document 2 does not provide any clue to the solution of a backlight problem associated with multi-directional simultaneous measurement which is a problem to be solved by the present invention.

Patent Document 3 proposes the use of a cylindrical convex mirror for expanding the image pickup range of a video camera placed along a conveyor for transporting fruit. This invention is similar to the present invention in that an image of an object reflected by a reflection mirror as well as a real image of the object is picked up. However, Patent Document 3 does not describe even an irradiation light source, and therefore does not give any clue to the solution of a backlight problem associated with multi-directional simultaneous measurement which is a problem to be solved by the present invention.

Patent Document 4 relates to a device for detecting defective parts by detecting leak light from an inspection surface of a printed-wiring board or the like, and describes a method for detecting light leaking through a printed-wiring board to be inspected when a light source is placed on the back side of the printed-wiring board. As described above, Patent Document 4 describes a technique for "utilizing" light from the opposite side of a camera, whereas the present invention deals with a technique for "avoiding" backlight from the opposite side of a camera. Therefore, the invention disclosed in Patent Document 4 has nothing in common with the present invention dealing with a technique for "avoiding" light from the opposite side of a camera. In this invention, light reflected by a defective part happens to be received by two or more mirrors arranged in different directions, but this does not give any clue to the solution of a backlight problem associated with multi-directional simultaneous measurement which is a problem to be solved by the present invention.

Patent Document 5 relates to a device for detecting a fluorescence image of a biological specimen having been subjected to, for example, electrophoresis by a CCD camera. When the size of a specimen is changed, the specimen needs to be moved toward or away from the camera. Therefore, a technique for compensating for the fluctuation of data caused by the difference in distance from a fluorescence excitation light source is described in Patent Document 5. In the case of this device, however, fluorescence is observed from only one direction, and in addition, the disadvantage of backlight is not perceived as a problem at all, although two light sources for irradiating a specimen with excitation light from two directions, that is, a bottom excitation light source 51 and a downward irradiating excitation light source 52 are shown in FIG. 2 in Patent Document 5. Therefore, although Patent Document 5 describes a fluorescence detection device, there is no description that gives a clue to the solution of problems to be solved by the present invention.

Patent Document 6 deals with an invention relating to a panoramic camera, that is, a technique for picking up a panoramic (360°) image around a camera. On the other hand, the present invention is directed to a multi-directional measurement device for picking up images of a specimen (object to be measured) placed at the center from various directions around the specimen. Considering that the positional relationship between a specimen and a camera is the reverse of that in the present invention, it is self-evident that Patent Document 6 has no bearing on the present invention. Although the camera disclosed in Patent Document 6 happens to use a polygonal reflection mirror for picking up a panoramic (360°) image around it, Patent Document 6 has nothing to do with a backlight problem to be solved by the present invention.

Patent Document 7 relates to a technique to be used for a device, such as a security camera, for picking up images of an object from one direction by simultaneously irradiating the object with light from three or more directions. More specifically, the frequencies (i.e., wavelengths) of irradiation light are made different among irradiation directions, and in addition, the filter of each pixel of a detector provided in a camera is selected so as to transmit any one of frequencies (wavelengths) different among irradiation directions. This makes it possible to acquire three or more images of an object different in irradiation direction while the object is simultaneously irradiated from three or more directions. The obtained images different in irradiation direction are weighted. There is some relation between Patent Document 7 and the present invention in multi-directional "illumination". However, Patent Document 7 discloses a unidirectional image pickup device and does not describe a backlight problem at all, whereas the present invention deals with a problem associated with multi-directional image pickup. In FIG. 1 of Patent Document 7, a camera happens to be pointed toward a light source, but it is not perceived as a problem in Patent Document 7. Therefore, it cannot be said that Patent Document 7 deals with a backlight problem, although the number of observation directions is only one. For this reason, it can be hardly said that the description of Patent Document 7 gives a clue to the solution of a backlight problem associated with multi-directional observation.

Patent Document 8 describes an invention relating to an endoscope. In Patent Document 8, image pickup using irradiation light having different wavelengths and a fluorescence image pickup device are described, and therefore, a fluorescence excitation light source is of course described. However, there is no description about multi-directional observation and a backlight problem caused by excitation light emitted from the fluorescence excitation light source. For this reason, Patent Document 8 does not at all give a clue to the solution of a backlight problem associated with multi-directional observation which is a problem to be solved by the present invention.

Patent Document 9 discloses backside illumination during fluorescence measurement. More specifically, a fluorescence excitation light source is arranged so as to be brought into contact with the back surface of a biological specimen so that the light source cannot be seen from a camera. That is, the light source is hidden by a specimen itself. This technique enables backside illumination in unidirectional observation, but definitely cannot be used in multi-directional observation. Further, strong light enters a detector when a specimen is removed. Therefore, the invention disclosed in Patent Document 9 is absolutely different from the present invention because the present invention is directed to a structure capable of preventing direct light from a light source from entering a detector regardless of the presence or absence of a specimen.

Patent Document 1: US Patent Application Publication No. 20050201614
Patent Document 2: JP-A-2001-330915
Patent Document 3: JP-A-10-124648
Patent Document 4: JP-A-3-111745
Patent Document 5: JP-A-2003-287497
Patent Document 6: JP-A-8-125835
Patent Document 7: WO 2007/108070
Patent Document 8: JP-A-2005-13611
Patent Document 9: U.S. Pat. No. 6,922,246

SUMMARY OF THE INVENTION

It is therefore an object of the present invention to provide a biological image acquisition multi-directional simultaneous observation device capable of avoiding projection of a light source onto a detector and unsharpening of images caused by an illumination backlight problem.

In general, illumination for biological image measurement is divided into two categories; one is illumination for external image acquisition, and the other is illumination for fluorescence excitation. Illumination for external image acquisition is necessary regardless of whether biological images to be measured are fluorescence images or luminescence images, because external images are superposed on fluorescence images or luminescence images acquired separately from the external images. As a matter of course, illumination for fluorescence excitation is required only for fluorescence image pick up.

In the case of multi-directional simultaneous image pickup, a backlight problem occurs in any one of image pickup directions in both cases of the above-described two types of illumination. Therefore, there is a necessity to avoid disadvantage caused by a backlight problem. However, in Patent Documents 1 to 9, there is no description about an illumination backlight problem.

In order to achieve the above object, the present invention is directed to a biological image acquisition device comprising: a specimen support on which a biological specimen is to be placed; a two-dimensional detector; an image pickup optical system which leads, to the two-dimensional detector, light traveling in a direction toward the two-dimensional detector from a sample placed on the specimen support and light traveling in another direction from the specimen to form images of these lights on the two-dimensional detector; a light source system arranged outside a field of view of the two-dimensional detector in order to irradiate a specimen placed on the specimen support with light; and an image display device for displaying images picked up by the two-dimensional detector. The field of view of the two-dimensional detector is formed by the image pickup optical system.

The word "light traveling in a direction toward the two-dimensional detector" refers to light traveling in a direction in which the two-dimensional detector can directly receive light.

In the present invention, the light source system is arranged outside the field of view of the two-dimensional detector formed by the image pickup optical system to avoid an illumination backlight problem for multi-directional observation, that is, to prevent the two-dimensional detector from directly receiving strong illumination light emitted from a light source. If the two-dimensional detector directly receives light emitted from a light source, very strong direct light from the light source causes so-called blooming that is a phenomenon in which appropriate pixels of a two-dimensional detector such as a COD are saturated, and in addition, excess charge spills over into many adjacent pixels so that not only the saturated pixels but also adjacent pixels in a wide range become unable to perform image pickup. Particularly, in the case of external image observation, wavelength components of a light source are led to the detector without filtering, and therefore, if direct light from the light source enters the detector, blooming is likely to occur. On the other hand, in the case of fluorescence image observation, wavelength components contained in a light source are removed using a filter before entering the detector. Therefore, even when direct light from a light source enters the detector, only leak light enters the detector because the cut-off rate of the filter is not 100%, and such leak light does not usually cause blooming. However, even in such a case, unnecessary light spots appear in part of measured data, which makes it difficult to identify target fluorescence emitted from a specimen. Therefore, the present invention takes measures to prevent the two-dimensional detector from receiving direct light from a light source during both external image observation and fluorescence image observation.

As described above, according to the present invention, it is possible to provide a multi-directional biological image acquisition device capable of avoiding projection of a light source onto a detector and unsharpening of images which are caused by a backlight problem.

In the case of conventional unidirectional (not multi-directional) image pickup, the above-described backlight problem associated with the use of a light source for external illumination or a fluorescence excitation light source does not occur. However, it has been found that, in the case of a multi-directional biological image acquisition device for simultaneously picking up images of a specimen from at least two opposite directions, for example, from above and below a specimen, some problems occur depending on the position of an irradiation light source. The present invention is completed as a result of extensive studies on means for avoiding such problems.

The means for avoiding such problems prevents direct light from a light source for external image acquisition and a fluorescence excitation light source from entering a CCD by arranging these light sources at positions outside the range of direct and indirect field of view of the camera as shown in FIGS. 3A and 3B. Here, the range of indirect field of view means the range of field of view projected onto the two-dimensional detector through an optical system such as a reflection mirror. In this way, it is possible to avoid the entry of direct irradiating light into a CCD also in the case of a device for simultaneously picking up images of a specimen from two opposite directions, and therefore, it is possible to construct a biological image acquisition device making full use of advantages of multi-directional image pickup.

As another means for avoiding the entry of direct light from a light source into a CCD, a method using "indirect illumination of specimen" instead of direct illumination of a specimen with a light source was also studied. In this case, images of a specimen are picked up by irradiating the specimen with light diffusely-reflected by a scattering plate or walls in order to avoid the entry of direct light from a light source into a CCD. However, it has been found as a result of testing that this means is disadvantageous for the following reason. In the case of indirect illumination, light reflected by a specimen (i.e., light to be measured) reaches a CCD through the following route: light source→scattering plate→specimen CCD. However, if the scattering plate is present in the above-described direct or indirect field of view of a camera, there is also light (interfering light) reaching a CCD through the following route: light source→scattering plate→CCD. In this case, when the diffuse reflection mirror is regarded as a light source, direct light from the diffuse reflection mirror reaches a CCD, that is, light stronger than light to be measured reaches a CCD.

The obtained key to the solution of the problems to be solved by the present invention can be more precisely expressed as follows: the biological image acquisition device according to the present invention needs to satisfy the requirement that "the number of diffuse reflections of light reflected by a specimen and then reaching a CCD (i.e., light to be measured) is the same as or less than the number of diffuse reflections of interfering light". For example, in the case of an embodiment shown in FIG. 1, a specimen is first illuminated with a light source directly, and then light reflected by the specimen (or fluorescence) enters a CCD as "light to be measured". On the other hand, in the case of interfering light, even when walls or the like are illuminated with a light source, light diffusely-reflected by the walls or the like enters the CCD, and therefore, the number of reflections of interfering light is the same as or less than the number of reflections of light to be measured. Ideally, it is preferred that surrounding walls are not illuminated with a light source, but this is virtually impossible. Therefore, surrounding walls are made of a material having a reflection factor as low as possible to reduce reflected light.

As a result, it has been found that clear images of a specimen isolated from their surrounding can be picked up by a detector by removing light scattered by objects other than the specimen, such as walls near the specimen, to prevent such scattered light from reaching the detector.

The key to the solution of the problems to be solved by the present invention can be again summarized based on the concept of the number of reflections as follows: the number of reflections of "light to be measured" reflected by the specimen can be made less than or at most the same as the number of reflections of "interfering light" reflected by walls or the like by arranging an irradiation light source outside the range of direct and indirect field of view of a camera. As a result, it is possible to avoid problems caused by backlight such as degradation of images and projection of a light source onto a camera, thereby making it possible to obtain clear images of a specimen.

The number of the two-dimensional detector is preferably only one.

In a case where multi-directional observation images of light from a specimen are simultaneously acquired, lights traveling in different directions may be formed into images on one two-dimensional detector or on two or more two-dimensional detectors. However, the use of only one two-dimensional detector simplifies the structure of the biological image acquisition device, thereby reducing production cost.

It is to be noted that two or more two-dimensional detectors may be provided. In this case, it is preferred that the two-dimensional detectors are arranged at such positions that they directly receive lights traveling in directions different from each other from a specimen placed on the specimen support and that the image pickup optical system is provided per each of the two-dimensional detectors. In this case, it is possible for each of the two-dimensional detectors to pick up lights traveling in two or more directions from the specimen (e.g., in a case where two two-dimensional detectors are arranged so that each of the two-dimensional detectors can pick up lights traveling in two different directions, images observed from four directions can be acquired). This makes it possible to reduce production cost as compared to a case where the two-dimensional detector is provided in every observation direction.

A preferred example of the light source system for arranging a light source outside the range of field of view of the two-dimensional detector is as follows. When the two-dimensional detector is arranged at such a position that it picks up images from a direction perpendicular to a surface of the specimen support on which a specimen is to be placed, the light source system includes a light source holder holding two or more light sources, and the light source holder holds light sources for acquiring external images or fluorescence excitation light sources in a plane perpendicular to the body axis of a biological specimen placed on the specimen support, and the image pickup optical system includes a mechanism for inserting, between a specimen and the two-dimensional detector, a filter, which transmits only a fluorescence wavelength while cutting off excitation light wavelength components, only during fluorescence image pickup.

A more specific example of the light source system includes one having a light source holder holding excitation light sources on the circumference of a circle whose center is located on an extension of the body axis of a biological specimen placed on the specimen support.

The circumference may comprise two or more concentric circumferences different in radius. In this case, it is possible to arrange more various excitation light sources that emit light having different wavelengths without increasing the size of the light source holder. This makes it possible to arrange light sources that emit light having various wavelengths that excite different fluorochromes, thereby expanding the range of excitation wavelengths options.

Further, the light source system may further include: a support mechanism which supports the light source holder so that the light source holder is capable of rotating around an axis passing through the center of the circumference on which light sources for external image pickup or fluorescence excitation light sources are held; and a driving system which rotates the light source holder. In this case, by allowing the light source holder to hold various light sources that emit light having different wavelengths that excite various different fluorochromes, it is possible to illuminate a biological specimen with a light source that emits light having a wavelength suitable for intended use from any position.

The light source for external illumination included in the light source system is necessary to pick up external images of a biological specimen by the two-dimensional detector because luminescence images or fluorescence images of the biological specimen are superposed on the external images of the biological specimen to make a relation between the positions of light spots in the images and the positions where luminescence or fluorescence is emitted in the biological specimen. The light source for external illumination can be realized simply by intentionally not removing wavelength components of illumination light by a filter during external image measurement, and therefore, a light source used exclusively for external illumination may be provided or a fluorescence excitation light source may also be used as a light source for external illumination.

One example of the image pickup optical system includes a reflection mirror that leads the light of image of a site whose image cannot be directly picked up by the two-dimensional detector to the two-dimensional detector by reflection. This structure makes it possible to increase the number of multi-directional images of a specimen simultaneously picked up by the two-dimensional detector by increasing the number of reflection mirrors.

Further, the image pickup optical system preferably includes an auxiliary imaging lens that compensates for the difference in optical path length between lights of two or more images formed on the two-dimensional detector.

A typical embodiment of the present invention will be described with reference to FIG. 1.

A biological image acquisition device shown in FIG. 1 is intended to simultaneously observe a biological specimen 4 such as a small animal (typically, a mouse) placed on a transparent specimen support 2 from two directions, from above and below. More specifically, the biological image acquisition device is configured to allow a common main image forming lens 8 arranged above the biological specimen 4 to form images of the biological specimen 4 observed from above and below onto a common two-dimensional detector (CCD camera) 6.

The back-side image of the biological specimen 4 is led to the common two-dimensional detector 6 by reflection from two reflection mirrors M1 and M2 so that such front-side (0°)

and back-side (180°) images of the biological specimen 4 as shown in FIG. 2 are simultaneously displayed on the two-dimensional detector 6. The back-side image displayed on the two-dimensional detector 6 is slightly smaller than the front-side image because the distance from the back-side image is longer than that from the front-side image. However, the magnification percentage of the back-side image displayed on the two-dimensional detector 6 can be finally corrected. Further, the distance (optical path length) between the back-side image and the main image forming lens 8 is different, due to the reflection mirrors, from the distance (optical path length) between the front-side image and the main image forming lens 8, and therefore, the back-side image displayed on the two-dimensional detector 6 is blurred. However, focus adjustment is achieved by inserting an auxiliary concave lens 12 so that blurring is corrected.

Meanwhile, such a biological image acquisition device includes a light source system for illuminating the biological specimen 4 for external image pickup or fluorescence excitation. In a case where multi-directional images of the biological specimen 4 are acquired in such a manner as described above, there is a case where a light source of the light source system arranged on the opposite side of the biological specimen 4 from the two-dimensional detector 6 is projected onto the two-dimensional detector 6. This occurs when, for example, a light source is arranged on the lower side of the biological specimen 4 to irradiate the back side of the biological specimen 4 with light to pick up the back-side image of the biological specimen 4. In this case, direct light from the light source enters the two-dimensional detector 6 so that problems such as blooming occur. Further, even when a light source is arranged on the same side as the two-dimensional detector 6, there is a case where light from the light source is reflected by a reflection mirror for multi-directional observation and then enters the CCD camera. Also in this case, direct light from the light source enters the two-dimensional detector 6 through the reflection mirror. In the case of a conventional biological image acquisition device for observing a biological specimen from only one direction, a light source is not arranged so as to be opposed to a camera and no reflection mirrors are used, and therefore, such a problem as described above does not occur.

In order to solve the above problem, in the case of the embodiment shown in FIG. 1, light source units S1 to S4 and S1' to S4' of the light source system for multi-directional irradiation are arranged at positions outside the direct field of view of the two-dimensional detector 6 formed without reflection mirrors and the indirect field of view of the two-dimensional detector 6 formed by reflection mirrors. The layout of the light source units S1 to S4 and S1' to S4' is more specifically shown in FIGS. 3A and 3B.

FIGS. 3A and 3B are diagrams showing an embodiment of a biological image acquisition device capable of observing a biological specimen from three directions (0° (front side), 144°, and 212°). FIG. 3A is a diagram of the biological image acquisition device viewed from a direction orthogonal to the body axis of the animal 4 as a biological specimen, and FIG. 3B is a diagram of the biological image acquisition device viewed from a direction parallel to the body axis of the animal 4.

In the biological image acquisition device shown in FIG. 3, the lens 8 and the two-dimensional detector 6 are arranged directly above the animal 4, and the two reflection mirrors M1 and M2 are arranged obliquely below the animal so that images of the animal observed from the directions of 144° and 212° are formed onto the common two-dimensional detector 6. Therefore, the biological image acquisition device shown in FIG. 3 is configured to be able to observe the animal 4 from three directions, including the front-side (0°) direction, in total.

The light source system for irradiating the biological specimen 4 with light from various directions includes a light source holder 14a holding the light source units S1 to S4 at regular intervals on the circumference of a circle whose center is located on a head-side extension of the body axis of the biological specimen 4 and a light source holder 14b holding the light source units S1' to S4' at regular intervals on the circumference of a circle whose center is located on a tail-side extension of the body axis of the biological specimen 4.

In order to prevent backlight, the positioning of these light source units S1 to S4 and S1' and S4' is important. In FIGS. 3A and 3B, hatched areas 16 and 18 represent a "field of view of the two-dimensional detector 6 in multi-directional observation". The triangular hatched area 16 below the lens 8 represents a direct field of view of the two-dimensional detector 6. The direct field of view of the two-dimensional detector 6 is the same as that in the case of conventional unidirectional observation. However, this embodiment includes the reflection mirrors M1 and M2, and therefore, there is an indirect field of view of the camera formed by the reflection mirrors M1 and M2. The indirect field of view of the two-dimensional detector 6 is represented by the hatched area 18.

If the light source units are present within the hatched area in FIGS. 3A and 3B, that is, within the direct field of view 16 or the indirect field of view 18, direct light from the light source units enters the two-dimensional detector 6 so that problems such as blooming occur. Therefore, in order to prevent direct light from the light source units S1 to S4 and S1' to S4' from entering the two-dimensional detector 6, as shown in FIG. 3A, the light source units S1 to S4 and S1' to S4' are obliquely arranged with respect to the biological specimen 4 at positions outside the direct field of view 16 and the indirect field of view 18 of the two-dimensional detector 6 to emit light toward the biological specimen 4 from oblique directions.

Further, the light source units S1 to S4 and S1' to S4' may be arranged on the circumference of a circle whose center is located on an extension of the body axis of the animal 4 to improve the uniformity of irradiation. Further, the light source holders 14a and 14b may be arranged on the head side and tail side of the biological specimen 4 so as to sandwich the biological specimen 4 to improve the uniformity of irradiation and reduce shadows on the biological specimen 4. The direct and indirect field of view of the two-dimensional detector in the case of the embodiment shown in FIG. 1 is slightly different from that of the embodiment shown in FIG. 3, but can be determined in the same manner as in the case of the embodiment shown in FIG. 3 based on the principles described above with reference to FIG. 3.

Each of the light source units S1 to S4 and S1' to S4' of the light source system will be described with reference to FIG. 1 as follows. Each of the light source units S1 to S4 and S1' to S4' of the light source system includes light sources A, B, and C.

The light source A is an illumination light source, such as a white light-emitting diode (hereinafter, also referred to as "white LED"), for acquiring external images of the specimen. Therefore, external images of the specimen 4 observed from the directions of 0° and 180° can be acquired by turning on the light sources A held by the light source holder 14a at four positions.

The light sources B and C are fluorescence excitation light sources that emit excitation lights different in wavelength from each other. Each of the excitation light sources B and C includes a light-emitting device such as a laser diode, and light emitted from the light-emitting device passes through an interference filter and illuminates the specimen. During fluorescence image pickup, a fluorescence-side filter 10 is inserted between the specimen 4 and the imaging lens 8. The fluorescence-side filter 10 is selected so that all the wavelength components of light that pass through the excitation-side filter can be cut off. This makes it possible to prevent disturbance caused by scattering of irradiating light having an excitation wavelength, thereby allowing only a fluorescence wavelength component generated by excitation with light having an excitation wavelength to be formed into a 0° fluorescence image and a 180° fluorescence image by the lens 10 onto the CCD 6.

It is to be noted that in FIGS. 1 and 3, the light source holders 14a and 14b are shown only by their circumferential parts holding the light source units S1 to S4 and S1' to S4'.

Likewise, in the case of the embodiment shown in FIG. 3, four light sources A are turned on to acquire external images of the specimen 4 observed from the directions of 0°, 144°, and 212°, and four light sources B or C are turned on to acquire fluorescence images of the specimen 4 observed from the directions of 0°, 144°, and 212°.

According to the present invention, a light source of a light source system required to acquire external images or fluorescence images of a biological specimen is arranged outside the field of view of a two-dimensional detector formed by an image pickup optical system to avoid an illumination backlight problem in a biological multi-directional observation device. Therefore, it is possible to provide a biological multi-directional observation device capable of preventing degradation of images caused by projection of direct light from a light source onto a two-dimensional detector and blooming resulting from backlight to obtain clear multi-directional images of a biological specimen. Further, the multi-directional observation device according to the present invention is capable of avoiding the above-described backlight problem while simultaneously and parallelly performing observation of luminescence or fluorescence images or external images of a biological specimen from various different directions with ease because lights traveling in two or more directions different from each other from the biological specimen are simultaneously formed into images by an image pickup optical system onto a two-dimensional detector.

BRIEF DESCRIPTION OF THE DRAWINGS

FIG. 4B is a graph showing one example of the relationship among the emission spectrum of an excitation light source, the transmission spectrum of an interference filter, and the transmission spectrum of a fluorescence-side filter.

Figure 1:
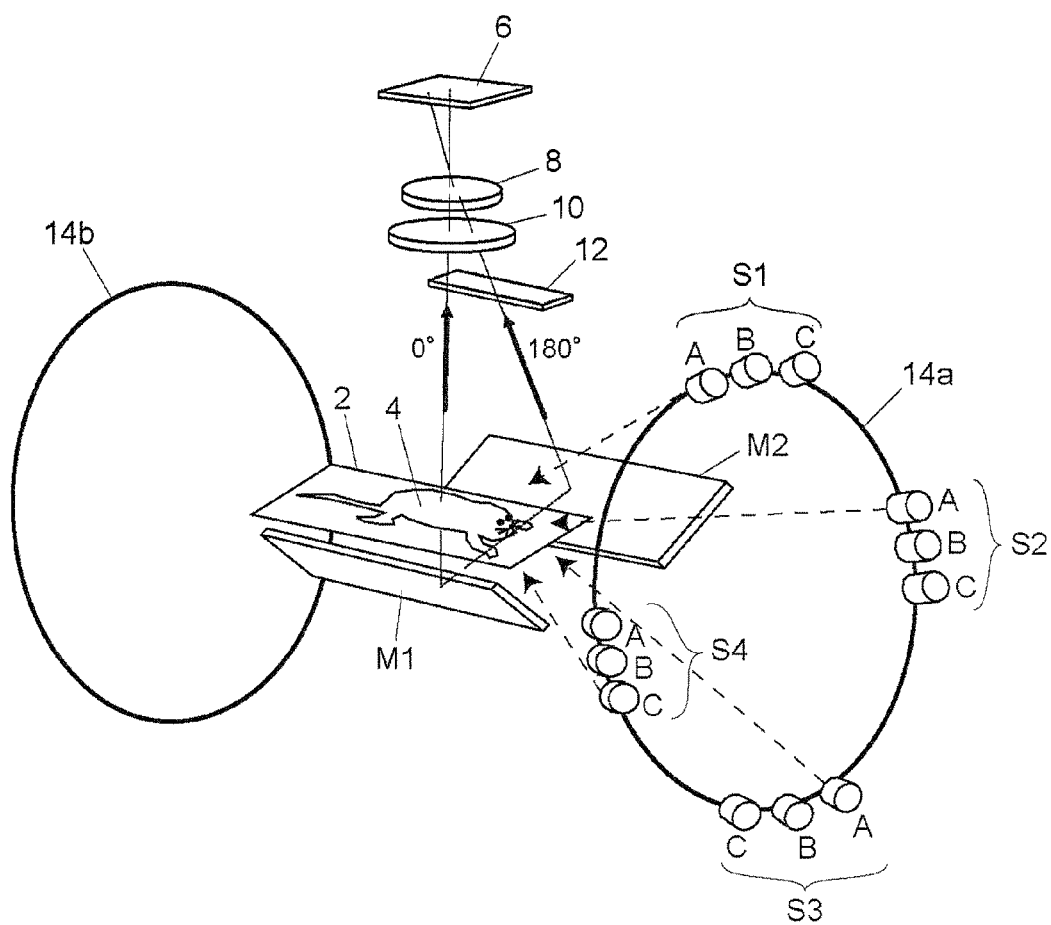
FIG. 1 is a schematic diagram showing the structure of one embodiment of a biological image acquisition device according to the present invention.

DESCRIPTION OF THE REFERENCE NUMERALS 2 specimen support
4 biological specimen
6 two-dimensional detector
8 main image forming lens
10 fluorescence-side filter
12, L1 to L5 auxiliary imaging lens
14a, 14b, 24, 38, 46 light source holder
16 direct field of view of two-dimensional detector
18 indirect field of view of two-dimensional detector
18A indirect field of view projected onto two-dimensional detector through reflection mirror M1 when concave mirrors are used
18B indirect field of view projected onto two-dimensional detector through reflection mirror M2 when concave mirrors are used
18C distribution map of light beams impinging on reference surface after reflection from reflection mirror M1
18D distribution map of light beams impinging on reference surface after reflection from reflection mirror M2
28 continuous-spectrum light source
30 converging lens
32a, 32b, 36 optical fiber
34 interference filter disk
34a interference filter
40 stepper motor
42 pulley
44 belt
A to F light sources
M1 to M5 reflection mirrors
S1 to S5 light source units

DETAILED DESCRIPTION OF THE INVENTION

Embodiment 1

One embodiment of a biological image acquisition device according to the present invention will be described as follows. FIG. 1 is a schematic view showing the structure of an embodiment of a device capable of observing a biological specimen from two directions, from above and below.

A biological specimen (small animal) 4 is placed on a transparent specimen support 2. A two-dimensional detector 6 such as a CCD camera is arranged directly above the biological specimen 4. A main image forming lens 8 is arranged on the detection surface-side of the two-dimensional detector 6. If necessary, a fluorescence-side filter 10, which transmits only a fluorescence component emitted from the biological specimen 4, is arranged between the main image forming lens 8 and the biological specimen 4. Reflectors M1 and M2 for leading the light of back-side (180° direction) image of the biological specimen 4 to the main image forming lens 8 are arranged on the lower side of the specimen support 2.

A light source system for irradiating the biological specimen 4 with light includes a light source holder 14a holding light source units S1 to S4 at regular intervals on the circumference of a circle whose center is located on a head-side extension of the body axis of the biological specimen 4 and a light source holder 14b holding light source units S1' to S4' (not shown) at regular intervals on the circumference of a circle whose center is located on a tail-side extension of the body axis of the biological specimen 4. It is to be noted that in FIG. 1, the light source holders 14a and 14b are shown only by their circumferential parts holding the light sources S1 to S4 and S1' to S4'.

Figure 2:
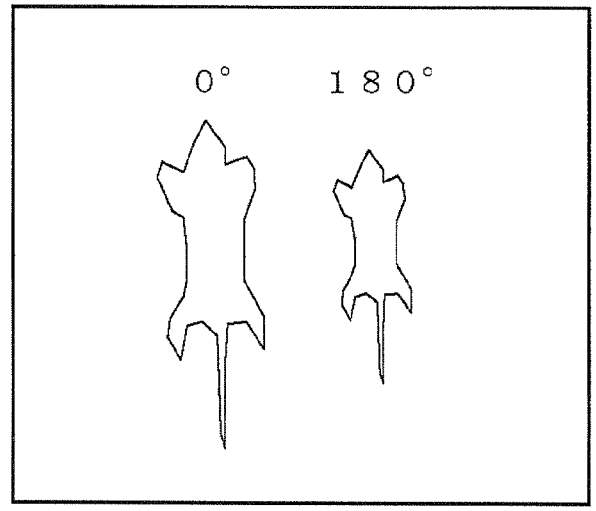
FIG. 2 is a diagram showing one example of images picked up by the biological image acquisition device shown in FIG. 1.

Such a structure as described above makes it possible for the two-dimensional detector 6 to simultaneously pick up such front-side (0°) and back-side (180°) images as shown in FIG. 2. More specifically, the light of front-side image of the biological specimen 4 and the light of back-side image of the biological specimen 4 reflected by the reflection mirrors M1 and M2 are formed into images by the imaging lens 8 arranged under the two-dimensional detector 6, and these two images are simultaneously displayed on the two-dimensional detector 6. The back-side image displayed on the two-dimensional detector 6 is slightly smaller than the front-side image because the optical path of the back-side image is longer than that of the front-side image. However, the magnification percentage of the back-side image displayed on the two-dimensional detector 6 can be finally corrected. Further, the optical path length of the back-side image, that is, the optical path length from the reflection mirror M1 through the reflection mirror M2 to the main image forming lens 8 is different from the optical path length of the front-side image formed by the main image forming lens 8, and therefore, the back-side image displayed on the two-dimensional detector 6 is blurred. However, insertion of a weak auxiliary concave lens 12 allows in-focus images observed from different directions to be displayed on the two-dimensional detector 6.

Figure 3A:
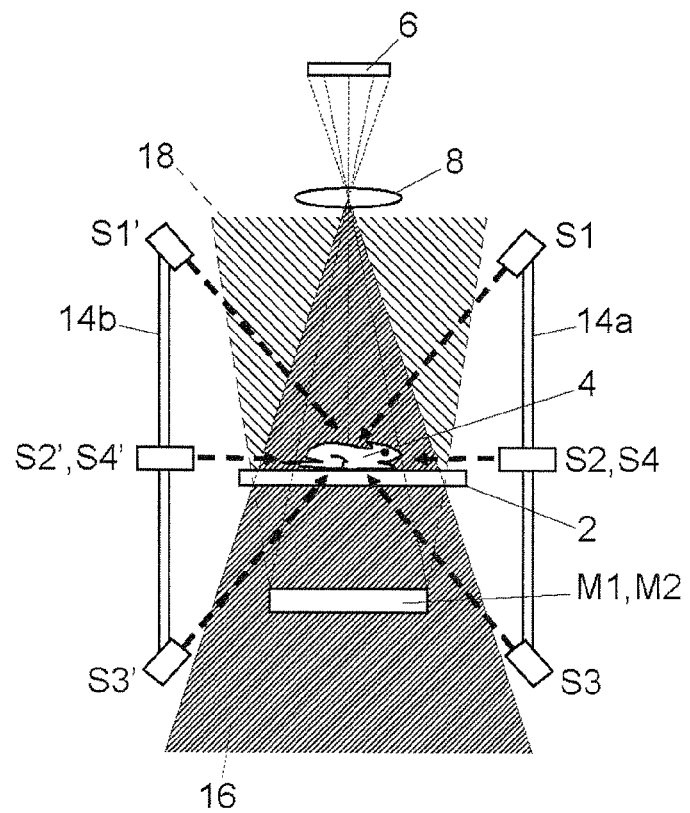
FIG. 3A is a diagram of a biological image acquisition device for explaining the positional relationship between the direct and indirect field of view of a two-dimensional detector and a light source system, which is viewed from a direction orthogonal to the body axis of a biological specimen.
Figure 3B:
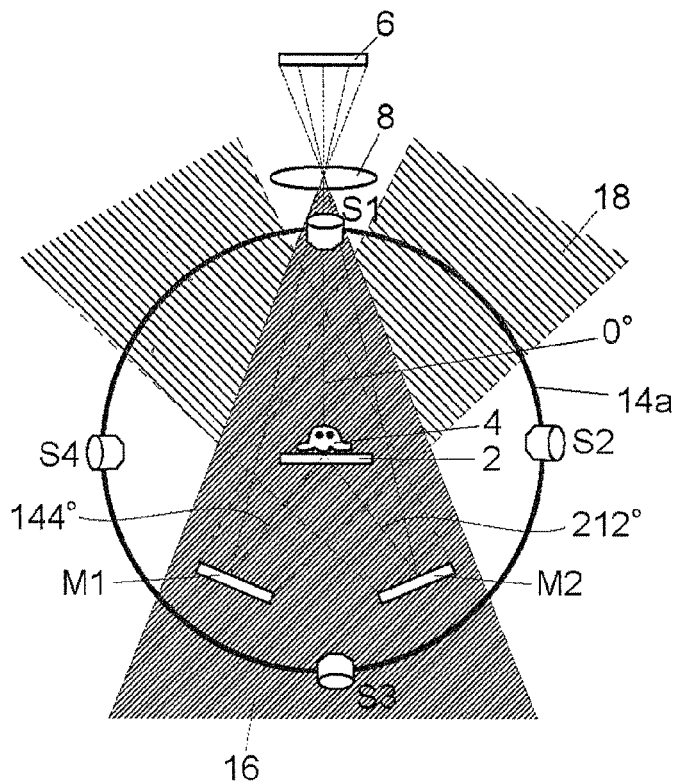
FIG. 3B is a diagram of a biological image acquisition device for explaining the positional relationship between the direct and indirect field of view of a two-dimensional detector and a light source system, which is viewed from a head side of a biological specimen.

FIGS. 3A and 3B show the positional relationship between the light source units S1 to S4 and S1' to S4' of the light source system and the field of view of the two-dimensional detector 6. In FIGS. 3A and 3B, a densely-hatched area 16 represents a direct field of view of the two-dimensional detector 6, and a sparsely-hatched area 18 represents an indirect field of view of the two-dimensional detector 6 formed by the reflection mirrors M1 and M2. It is to be noted that in the case of this embodiment shown in FIGS. 3A and 3B, the reflection mirrors M1 and M2 are arranged obliquely below the biological specimen 4 as an optical system for leading the light of image of the biological specimen 4 observed from a 144° direction and the light of image of the biological specimen 4 observed from a 212° direction to the main image forming lens 8. Therefore, in total, three images of the biological specimen 4 observed from three different directions, that is, one front-side (0°) image and two images observed from a 144° direction and a 212° direction can be simultaneously acquired by the two-dimensional detector 6. As shown in FIGS. 3A and 3B, the light source units S1 to S4 and S1' to S4' are obliquely arranged with respect to the biological specimen 4 at positions outside both the direct field of view 16 and the indirect field of view 18 of the two-dimensional detector 6. As described above, since the light source units S1 to S4 and S1' to S4' are not present within the range of the direct field of view 16 and the indirect field of view 18 of the two-dimensional detector 6, projection of direct light from the light source units S1 to S4 and S1' to S4' onto the two-dimensional detector 6 does not occur and thus problems caused by backlight, such as blooming, do not occur. It is to be noted that the positions of the reflection mirrors M1 and M2 are different between the embodiment shown in FIG. 1 and the embodiment shown in FIG. 3, but the positions of the light source units S1 to S4 and S1' to S4' are the same in both the embodiments shown in FIG. 1 and FIG. 3.

The direction of observation and the direction of irradiation are independent of each other, and therefore, a desired combination of the number of observation directions and the number of irradiation directions such as a combination of two-directional observation and two-directional irradiation, a combination of three-directional observation and four-directional irradiation, a combination of five-directional observation and five-directional irradiation, or the like can be selected when the device is designed. This is why the embodiments shown in FIG. 1 and FIG. 3 and an embodiment shown in FIG. 5 (which will be described later) are intentionally made different in combination of the number of observation directions and the number of irradiation directions.

It is to be noted that also in FIG. 3, the light source holders 14a and 14b are shown only by their circumferential parts holding the light source units S1 to S4 and S1' to S4'.

The light source units S1 to S4 and S1' to S4' will be described with reference to FIG. 1. Each of the light source units S1 to S4 and S1' to S4' includes light sources A to C. The light source A is a white LED which emits visible light ranging from 400 nm to 700 nm and has a spatial irradiation angle allowing the whole biological specimen 4 to be irradiated with light. The light sources B and C are both fluorescence excitation light sources, but are different in excitation wavelength. The light source B is, for example, a laser diode (hereinafter, also referred to as "LD") that emits light having a wavelength of 690 nm, and the light source C is, for example, an LD that emits light having a wavelength of 780 nm.

Figure 4A:
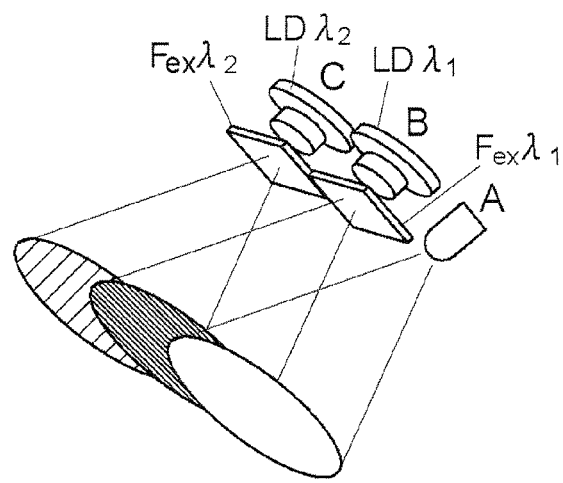
FIG. 4A is a perspective view schematically showing the structure of one example of a light source unit.

FIG. 4A is a diagram showing the structure of a specific example of each of the light source units S1 to S4 and S1' to S4'.

The light source A is a white LED for illuminating the biological specimen 4 to pick up external images of the biological specimen 4. The light sources B and C are fluorescence excitation light sources. More specifically, the light source B includes a light-emitting device $LD\lambda_1$ that emits excitation light having a wavelength of $\lambda_1$ and an excitation-side interference filter $Fex\lambda_1$ attached to the light-emitting side of the light-emitting device $LD\lambda_1$. The light source C includes a light-emitting device $LD\lambda_2$ using an LD that emits excitation light having a wavelength of $\lambda_2$ and an excitation-side interference filter Fex$\lambda_2$ attached to the light-emitting side of the light-emitting device LD$\lambda_2$. However, if necessary, each of the light sources B and C may further include a diverging lens (not shown) provided on the light-output side of the interference filter Fex$\lambda_1$ or Fex$\lambda_2$ to irradiate the whole biological specimen 4 with light. It is to be noted that selection among these three light sources A, B, and C shown in FIG. 4A can be performed simply by turning on/off each of them without mechanical switching. Therefore, the direction of irradiation (S1 to S4, S1' to S4') and the type of light source (A, B, C) are selected not by mechanical switching but by turning on/off each of the light sources A, B, and C of each of the light source units S1 to S4 and S1' to S4' arranged in different directions.

The properties of the excitation light source and the excitation-side interference filter will be described with reference to FIG. 4B as follows. FIG. 4B is a graph showing the relationship between the light-emitting device LD$\lambda_1$ of the light source B and the interference filter Fex$\lambda_1$ attached to the light-emitting side of the light-emitting device LD$\lambda_1$.

The light-emitting device LD$\lambda_1$ tends to be considered as a device that emits only light of single wavelength $\lambda_1$, but in reality, the light-emitting device LD$\lambda_1$ also emits weak light represented as a skirt portion around the peak of the emission spectrum thereof. The skirt portion of the emission spectrum of the light-emitting device LD$\lambda_1$ includes wavelength components that pass through the fluorescence-side filter 10 provided on the light-input side of the two-dimensional detector 6. Therefore, if the biological specimen 4 is irradiated with light including such wavelength components, such wavelength components as well as a fluorescence component emitted from the biological specimen 4 pass through the fluorescence-side filter 10 and then enter the two-dimensional detector 6. As a result, sensitivity for detection of fluorescence is lowered because stray light, containing leak light components other than fluorescence emitted from the specimen, overlaps fluorescence images picked up by the two-dimensional detector 6.

Therefore, in this embodiment, the interference filter Fex$\lambda_1$ for cutting off light having wavelengths within the skirt portion of the emission spectrum of the light-emitting device LD$\lambda_1$ is attached to the light-emitting side of the light-emitting device LD$\lambda_1$ to remove excitation light components within the pass band of the fluorescence-side filter 10 from light emitted from the light-emitting device LD$\lambda_1$. This makes it possible to allow only a fluorescence component emitted from the biological specimen 4 to pass through the fluorescence-side filter 10, thereby preventing the lowering of the ability to detect fluorescence due to contamination of images displayed on the two-dimensional detector 6 with stray light.

It is to be noted that the excitation light source has been described above with reference to the light source B but the light source C also has the same structure as the light source B.

The fluorescence excitation light source having such a structure as described above, that is, the fluorescence excitation light source having a laser diode LD or a light-emitting diode LED and an optical filter, such as an interference filter, attached to the LD or LED to cut off light having wavelengths within the skirt portion of the emission spectrum of the LD or LED is significantly effective at preventing the lowering of the ability to detect fluorescence due to the contamination of images displayed on the two-dimensional detector 6 with stray light.

It is to be noted that each of the embodiments shown in FIGS. 1 and 3 has two light source holders 14a and 14b, but the present invention is not limited thereto. For example, only one light source holder may be provided.

Further, in the above embodiments, each of the light source units S1 to S4 and S1' to S4' comprises light sources A to C. However, each of the light source units S1 to S4 and S1' to S4' may comprise one illumination light source A and one excitation light source B or C or may comprise only two excitation light sources B and C. That is, each of the light source units S1 to S4 and S1' to S4' may be configured depending on the intended use.

The operation of the biological image acquisition device shown in FIG. 1 during fluorescence image measurement will be described as follows.

First, only the illumination light sources A (white LEDs) of all the light source units S1 to S4 and S1' to S4' are turned on. At this time, the fluorescence-side filter 10 is not arranged in front of the main image forming lens 8. In this state, external images of the biological specimen 4 are acquired by the two-dimensional detector 6.

Then, the fluorescence-side filter 10 whose pass band is set so that the wavelength $\lambda_1$ (e.g., 690 nm) of light emitted from the light source B can be cut off is arranged in front of the main image forming lens 8, and then only the excitation light sources B of all the light source units S1 to S4 and S1' to S4' are turned on. In this state, fluorescence images of the biological specimen 4 excited by excitation light having a wavelength of $\lambda_1$ are acquired by the two-dimensional detector 6.

Then, the pass band of the fluorescence-side filter 10 arranged in front of the main image forming lens 8 is set so that the wavelength $\lambda_2$ (e.g., 780 nm) of light emitted from the light source C can be cut off, and then only the excitation light sources C of all the light source units S1 to S4 and S1' to S4' are turned on. In this state, fluorescence images of the biological specimen 4 excited by excitation light having a wavelength of $\lambda_2$ are acquired by the two-dimensional detector 6.

As shown in FIG. 2, two types of images, that is, a front-side image (0°) and a back-side image (180°) are acquired by the two-dimensional detector 6, and therefore, six types of images can be acquired in total by the above-described three times image pickup.

In the case of the above-described method in which fluorescence images are picked up by turning on the light sources B or C, all the light sources B or all the light sources C are turned on at the same time to pick up fluorescence images of the biological specimen 4 irradiated with excitation light from four directions at the same time. However, each of the four light sources B or each of the four light sources C may be turned on in turn. In this case, image pickup is performed every time the irradiation direction is changed, and therefore, two front-side and back-side fluorescence images can be acquired per each of the four different irradiation directions. Therefore, it takes longer time to pick up all the images, but more various fluorescence images can be acquired by changing the combination of the irradiation direction and the observation direction because the appearance pattern of fluorescence varies depending on the irradiation direction of excitation light.

On the other hand, in the case of luminescence image measurement, all the light sources are turned off when luminescence images are picked up, and only the light sources A are turned on when external images are picked up.

Embodiment 2

Figure 5:
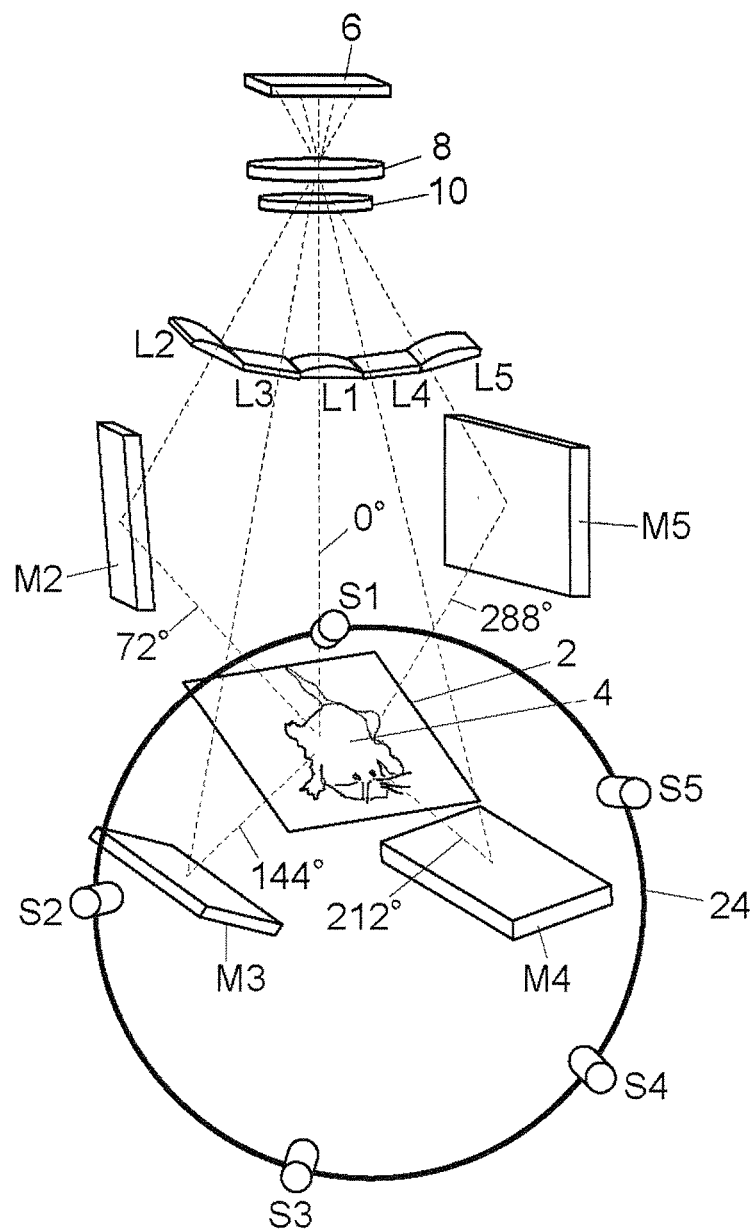
FIG. 5 is a schematic diagram showing the structure of a second embodiment of the biological image acquisition device according to the present invention.

An embodiment of a biological image acquisition device capable of simultaneously picking up images of a biological specimen from five directions will be described. FIG. 5 is a schematic view showing the structure of an embodiment of a biological image acquisition device capable of simultaneously observing a biological specimen from five directions.

The biological specimen (small animal) 4 is placed on the transparent specimen support 2. The two-dimensional detector 6, such as a CCD camera, is arranged directly above the biological specimen 4. The main image forming lens 8 is arranged on the detection surface-side of the two-dimensional detector 6. If necessary, the fluorescence-side filter 10, which transmits only a fluorescence component emitted from the biological specimen 4, is arranged between the main image forming lens 8 and the biological specimen 4. Reflectors M2, M3, M4, and M5 are arranged counterclockwise around the specimen support 2. The reflection mirrors M2 to M5 reflect the lights of images of the biological specimen 4 observed from the positions of 72°, 144°, 216°, and 288° (the front side (0 o'clock direction) of the biological specimen 4 is defined as 0°) so that the lights are led to the main image forming lens 8. Auxiliary imaging lenses L1 to L5 are arranged in optical paths from the reflection mirrors M2 to M5 to the main image forming lens 8 in order to correct defocusing caused by the difference in length among these optical paths. In this embodiment, the auxiliary lenses L1 to L5 constitute a mosaic lens.

A light source system for irradiating the biological specimen 4 with light includes a light source holder 24 holding light source units S1 to S5 at regular intervals on the circumference of a circle whose center is located on a head-side extension of the body axis of the biological specimen 4. The light source unit S1 is arranged so that the biological specimen 4 is irradiated with light emitted from a direction oblique to a 0° direction. The light source units S2 to S4 are arranged every 72° counterclockwise from the light source unit S1. That is, the light source units S2 to S4 are arranged at angles corresponding to the angles at which the biological specimen 4 is observed using the reflection mirrors M2 to M4. Each of the light source units S1 to S5 has the same structure as shown in FIG. 4, and therefore includes the light sources A to C. As in the case of the embodiment shown in FIG. 3, the light source holder 24 and the light source units S1 to S5 are arranged at positions outside both the direct field of view of the two-dimensional detector 6 and the indirect field of view of the two-dimensional detector 6 formed by the reflection mirrors M2, M3, M4, and M5. It is to be noted that in FIG. 5, the light source holder 24 is shown only by its circumferential part holding the light source units S1 to S5.

Figure 6:
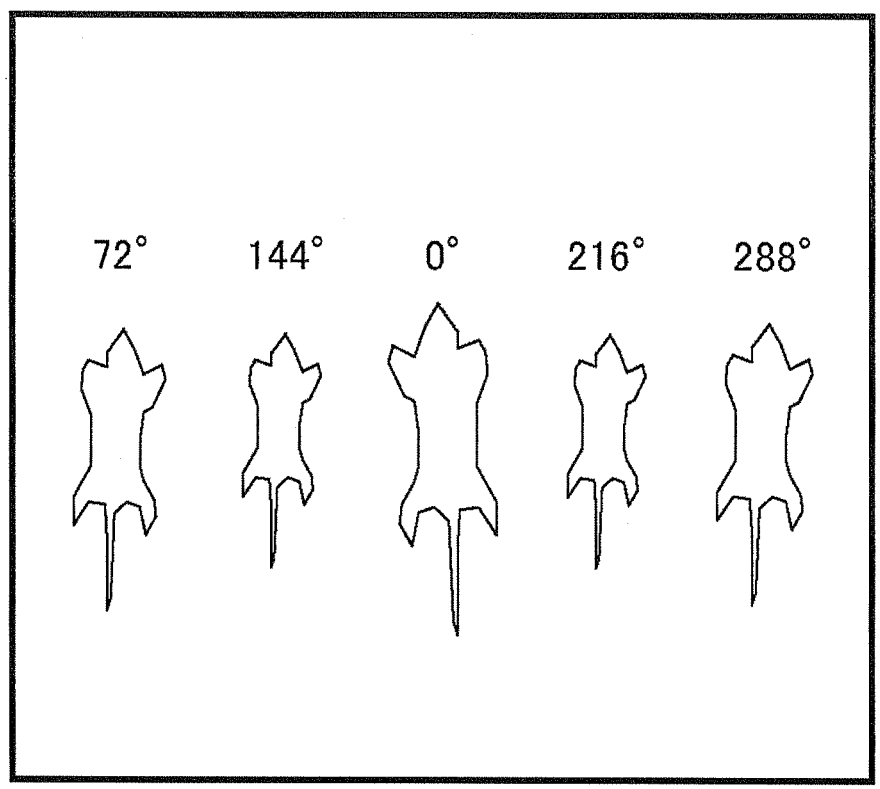
FIG. 6 is a diagram showing one example of images picked up by the biological image acquisition device shown in FIG. 5.

In the structure described above, the lights of images of the biological specimen 4 placed on the specimen support 2 observed from different angles other than 0°, that is, 72°, 144°, 216°, and 288° are reflected by the reflection mirrors M2, M3, M4, and M5, respectively and are formed into images by the imaging lens 8 onto the common two-dimensional detector 6. The lights from different observation angles reflected by the reflection mirrors M2, M3, M4, and M5 are different in optical path length from one another. Therefore, weak auxiliary imaging lenses L1 to L5 different in focal length from one another are inserted into the optical paths different in observation angle from one another in order to correct defocusing. As a result, as shown in FIG. 6, five images of the biological specimen 4 observed from five different directions are displayed on the two-dimensional detector 6.

In this embodiment, the light source system is constituted from one light source holder 24 provided on the head side of the biological specimen 4. However, the light source holder may be provided also on the tail side of the biological specimen 4. This makes it possible to more uniformly irradiate the biological specimen 4 with light from both the head side and tail side of the biological specimen 4, thereby reducing shadows.

Further, in this embodiment configured to acquire five images of the biological specimen 4 observed from five different directions, the light source holder 24 holds five light source units S1 to S5 so that the biological specimen 4 can be irradiated with light from angles corresponding to image pickup directions. However, the number of observation directions does not always need to be the same as the number of irradiation directions, and therefore, the light source holder 24 may hold four or less light sources or six or more light sources. Further, in this embodiment, the irradiation angles of the five light sources correspond with the observation angles but are not particularly limited. For example, the five light sources may be arranged on the circumference of the light source holder 24 in five directions of 36°, 108°, 180°, 252°, and 312°. In this case, each irradiation direction is midway between two observation directions. Therefore, for example, in the case of observation from a 0° direction, when the light sources arranged in a 36° direction and a 312° direction are turned on, the specimen is uniformly irradiated with light from the front side, and when only the light source arranged in a 180° direction is turned on, the specimen irradiated with light from the back side is observed from the opposite direction, that is, from a 0° direction. Likewise, in the case of observation from a 72° direction, the light sources arranged in a 108° direction and a 180° direction are turned on to irradiate the specimen with light from the front side and the light source arranged in a 252° direction is turned on to irradiate the specimen with light from the back side.

It is to be noted that the operation of the biological image acquisition device according to this embodiment during fluorescence image measurement is the same as that described above with reference to the first embodiment, and therefore a detailed description thereof is omitted here.

Figure 7:
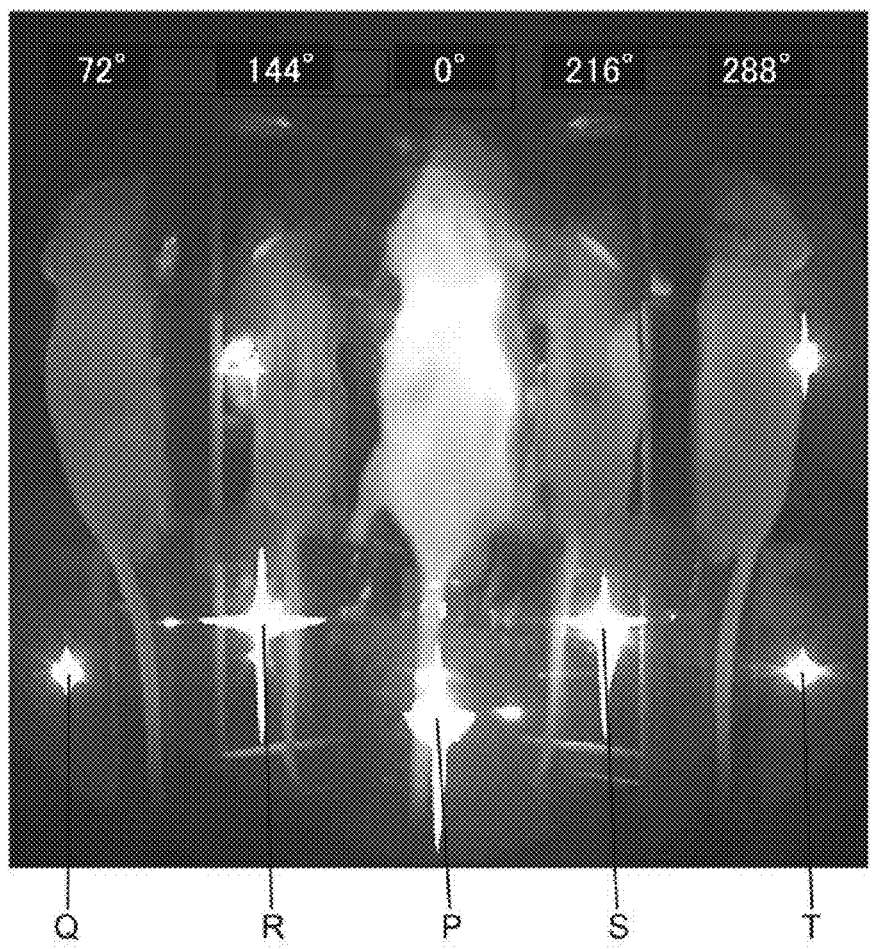
FIG. 7 is a photograph of images picked up by a two-dimensional detector in a state where light sources are present in the direct or indirect field of view of the two-dimensional detector.

FIG. 7 shows the external images of the biological specimen 4 picked up by a biological image acquisition device that is the same as the biological image acquisition device shown in FIG. 5 except that the light source units S1 to S5 are intentionally arranged at positions within the range of direct field of view or indirect field of view of the two-dimensional detector 6, which indicates what kind of problems may arise when such a biological image acquisition device is used. In FIG. 7, a "0°" image is an external image of the biological specimen 4 observed from directly above (i.e., from the front side), and "72°", "144°", "216°", and "288°" images are external images of the biological specimen 4 observed from the directions of 72°, 144°, 216°, and 288° counterclockwise from a 0° direction. These five external images shown in FIG. 7 were simultaneously picked up by the two-dimensional detector 6.

The 0° image is an image formed by the auxiliary lens L1 and the main image forming lens 8 and is directly picked up from above the biological specimen 4. In the case of image pickup from a 0° direction, light emitted from the light source units S1, S2, and S5 located on the upper side of the specimen support 2 is not a problem, but direct light emitted from the light source units S3 and S4 located on the lower side of the specimen support 2 passes through the transparent specimen support 2 and as a result appears as a bright light spot P on the two-dimensional detector 6.

In the case of image pickup from a 72° direction, light emitted from the light source unit S4 is reflected by the reflection mirror M2 and as a result appears as a light spot Q on the two-dimensional detector 6. In the case of image pickup from a 288° direction, light emitted from the light source unit S2 is reflected by the reflection mirror M5 and as a result appears as a light spot T on the two-dimensional detector 6. In the case of image pickup from a 144° direction, light emitted from the light source unit S5 is reflected by the reflection mirror M3 and as a result appears as a light spot R on the two-dimensional detector 6. In the case of image pickup from a 216° direction, light emitted from the light source unit S1 is reflected by the reflection mirror M4 and as a result appears as a light spot S on the two-dimensional detector 6. Particularly, as can be seen from FIG. 7, the light spots P, R, and S appearing in the images picked up from the directions of 0°, 144°, and 216° are in the shape of a cross larger than their original size. This is called "blooming". Blooming is a phenomenon that occurs when a light-receiving element receives extremely strong light and excess charge beyond saturation of the light-receiving element spills over into adjacent light-receiving elements. This phenomenon can be compared to lens halation that occurs in general photography when a photo is taken against the sun. When blooming occurs, an obtained image is partially damaged in an area where blooming occurs. Even when such extremely strong light does not cause blooming, an obtained image is not accurate, because a light spot appears in an area where light is not emitted in reality.

Therefore, as described above with reference to this embodiment, by arranging the light source units S1 to S5 at positions outside both the direct field of view and indirect field of view of the two-dimensional detector 6, it is possible to prevent such unnecessary light spots as described above from appearing in images picked up by the two-dimensional detector 6, thereby making it possible to acquire clear observation images.

In the above-described first and second embodiments, each of the excitation light sources of the light source system is a combination of a laser diode and an interference filter. However, the light source system used in the present invention may be configured so that the wavelength of excitation light emitted from one light-emitting device can be selectively switched using a filter whose pass band can be switched in order to distribute the excitation light to each of the excitation light sources. One example of the structure of such a light source system is shown in FIG. 8.

Figure 8:
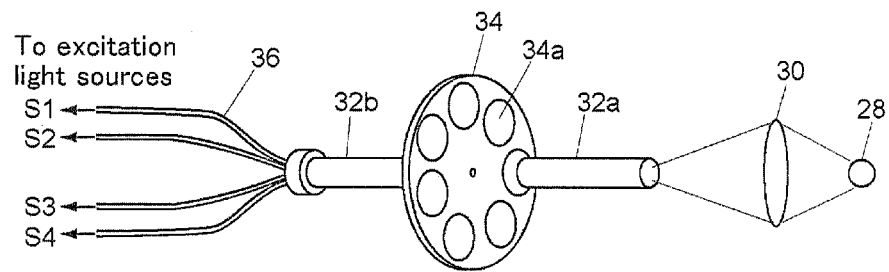
FIG. 8 is a diagram schematically showing the structure of another example of the light source system.

In the light source system shown in FIG. 8, a converging lens 30 is arranged on the light-emitting side of a light source 28 having a continuous emission spectrum, such as a halogen lamp, to lead continuous-spectrum light emitted from the light source 28 to the input end of an optical fiber 32a. On the output side of the optical fiber 32a, a filter disk 34 is provided. The filter disk 34 has a plurality of interference filters 34a different in pass band from one another, and the interference filters 34a are provided along the circumference of the filter disk 34. Therefore, selection among these interference filters 34a is performed by rotating the filter disk 34. This makes it possible to extract only light having a desired wavelength band from the continuous-spectrum light outputted from the optical fiber 32a. Also on the output side of the interference filter 34a of the filter disk 34, an optical fiber 32b is provided. The optical fiber 32b branches at some midpoint into two or more optical fibers 36 (in this case, into 4 optical fibers 36) for leading light to each of the excitation light sources. The distal end of each of the branched optical fibers 36 is led to the position of the light source B of each of the light source units S1 to S4 shown in FIG. 1 as a substitute for the light source B to emit light toward the specimen 4.

As described above, the light source 28 emits continuous-spectrum light, but a desired wavelength component is selectively extracted from the continuous-spectrum light by the selected interference filter 10 of the filter disk 34 and is then supplied to each of the excitation light sources. In the case of such a system, since the wavelength of excitation light is switched by the filter disk 34 that is a wavelength selection filter, two or more types of excitation lights different in wavelength can be emitted from one excitation light source. Therefore, each of the light source units needs only one excitation light source that emits excitation light toward the biological specimen 4. That is, each of the light source units S1 to S4 and S1' to S4' held by the light source holders 14a and 14b shown in FIG. 1 has light sources B and C as excitation light sources to emit two types of excitation lights different in wavelength, but when the light source system shown in FIG. 8 is used, only one of the light sources B and C is needed. However, in the case of the light source system shown in FIG. 8, light travels through the two or more optical fibers 36 at the same time, and therefore, it is impossible to turn on two or more light sources independently of each other at different timings, but it is possible to provide a variety of the filters 34a different in pass band in the filter disk 34, thereby easily increasing the number of excitation wavelength options. Alternatively, one of the filters of the filter disk 34 may be changed from an interference filter that transmits a specific wavelength to a neutral filter to attenuate light emitted from a halogen lamp to an appropriate level to use the attenuated light for external illumination. That is, the attenuated light can be used as a substitute for the light source A provided exclusively for external illumination by leading it to an irradiation position.

As described above, the light source for external illumination may be, for example, a white LED used as the light source A shown in FIGS. 1 and 4A or light obtained by attenuating light emitted from a halogen lamp shown in FIG. 8 to an appropriate level. Requirements for the light source for external illumination can be summarized as follows: 1) all or some of wavelength components of illumination light shall enter the two-dimensional detector without being removed by the filter 8 provided in front of the two-dimensional detector; and 2) if illumination light is as very bright as a fluorescence excitation light source, a detector saturates due to diffusely-reflected light from a specimen being too strong, and therefore, illumination light shall be sufficiently attenuated. Therefore, the light source for external illumination used in the present invention is not limited to the above examples as long as it satisfies these two requirements. For example, an LD or LED for fluorescence excitation may be used as a substitute for a white LED, that is, a fluorescence excitation light source may also be used as a light source for external illumination. In this case, it is necessary to emit weak light from the LD or LED to illuminate a specimen and to select the wavelength characteristics of the filter 8 provided in front of the two-dimensional detector so that the filter intentionally transmits some of wavelength components of light emitted from the LD or LED only during external illumination.

Figure 9:
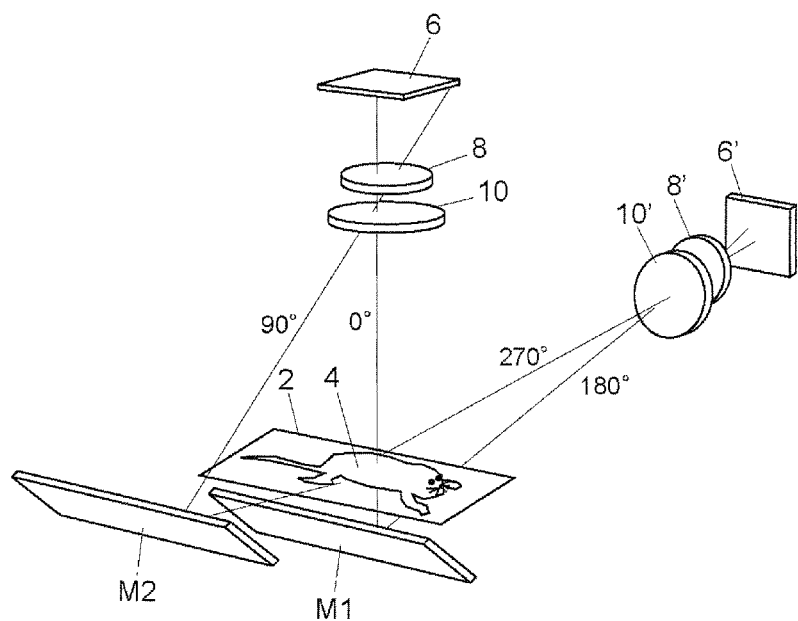
FIG. 9 is a diagram schematically showing the structure of an embodiment of a biological image acquisition device using two two-dimensional detectors.

Further, in the above first and second embodiments, multi-directional images of the biological specimen 4 are simultaneously acquired by picking them up by one two-dimensional detector, but as shown in FIG. 9, two or more two-dimensional detectors may be used to acquire multi-directional images of the biological specimen 4. In the case of an embodiment shown in FIG. 9, images observed from the directions of 0° and 90° are picked up by a first two-dimensional detector 6, and images observed from the directions of 180° and 270° are picked up by a second two-dimensional detector 6'. Although not shown in FIG. 9, all the light sources of the light source system for irradiating the biological specimen 4 with light need to be arranged at positions outside the direct field of view and indirect field of view (formed by reflection mirrors)

of both the two-dimensional detectors. That is, the embodiment shown in FIG. 9 also needs to be configured so that direct light from the light sources is not projected onto each of the two-dimensional detectors.

In the embodiment shown in FIG. 9, the two-dimensional detector 6' is provided at a position different from a position where the two-dimensional detector 6 located directly above the specimen support 2 is provided, and the reflection mirrors M1 and M2 are provided. Therefore, the front-side (0°) image of the biological specimen 4 is acquired by the two-dimensional detector 6 arranged directly above the biological specimen 4, the image of the biological specimen 4 observed from a 90° direction is acquired by picking up reflected light from the reflection mirror M2 by the two-dimensional detector 6, the back-side (180°) image of the biological specimen 4 is acquired by picking up reflected light from the reflection mirror M1 by the two-dimensional detector 6', and the image of the biological specimen 4 observed from a 270° direction is directly acquired by the two-dimensional detector 6'.

As described above, the light source system for irradiating the biological specimen 4 with light may be configured so that the variety of wavelengths of light emitted from the excitation light source can be increased to expand the range of excitation wavelength options. This makes it possible to select a light source that emits light having an optimum wavelength for each of various different fluorochromes. One example of such a light source system has been described above with reference to FIG. 8. Alternatively, the variety of excitation light sources provided in one light source unit may be further increased. Examples of such a light source system are shown in FIGS. 10 and 11.

Figure 10:
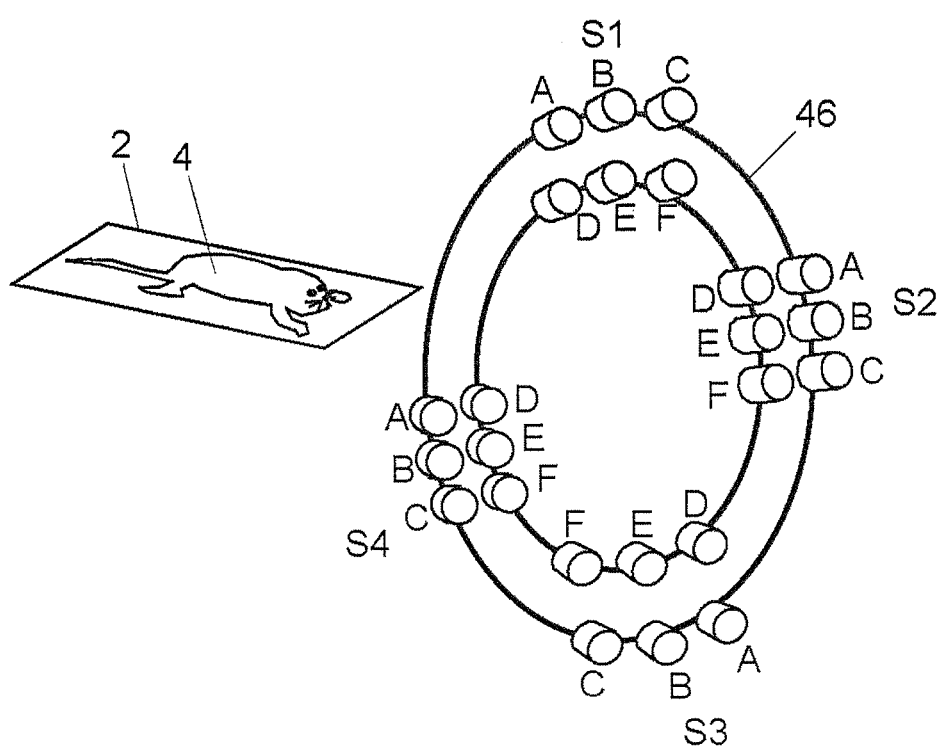
FIG. 10 is a diagram schematically showing the structure of a modified example of the light source system.

In the case of the example shown in FIG. 10, each of the light source units S1 to S4 includes six light sources A to F, and these light sources A to F are held by a light source holder 46 on the circumferences of two concentric circles. The light sources A to C of the light source units S1 to S4 are held on the circumference of a circle which is perpendicular to the plane of the specimen support 2 and whose center is located on a head-side extension of the body axis of the biological specimen 4. The light sources D to F are held on the circumference of a circle concentrically provided inside the circle, on the circumference of which the light sources A to C are held. In this case, a white LED may be used as the light-emitting part A for use in picking up the external images of the biological specimen 4, and LDs or LEDs may be used as the remaining light-emitting parts B to F for use in exciting fluorescence. By holding light sources on the circumferences of multiple circles by the light source holder 46 in such a manner as described above, it is possible to effectively utilize a space outside the direct field of view and indirect field of view of the two-dimensional detector (not shown) to arrange more various excitation light sources.

Figure 11:
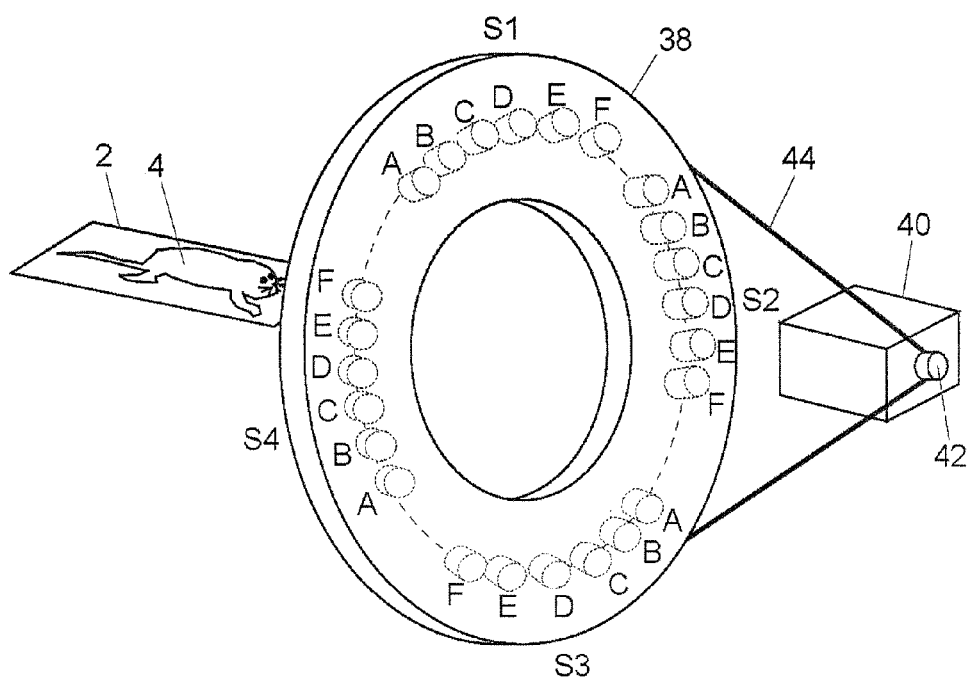
FIG. 11 is a diagram schematically showing the structure of another modified example of the light source system.

In the case of the example shown in FIG. 11, each of the light source units S1 to S4 includes six light sources A to F, and these light sources A to F are held by a light source holder 38 on the circumference of a circle which is perpendicular to the plane of the specimen support 2 and whose center is located on a head-side extension of the body axis of the biological specimen 4. The light sources A to F of each of the light source units S1 to S4 are arranged in line on the same circumference. The light source holder 38 is supported by a support system (not shown) so as to be able to rotate around an axis passing through the center of the circumference on which the light source units S1 to S4 are held. The light source holder 38 is configured to be rotatably driven by a driving system constituted from, for example, a stepper motor 40 and a pulley 42 through a belt 44. In the case of this example, a light source that should be turned on can be moved to a desired position by driving the stepper motor 40, and therefore, light having a desired wavelength can be emitted from a desired position even when a plurality of light sources are arranged on the same circumference. It is to be noted that in FIG. 11, the four light source units S1 to S4 are arranged on the same circumference at regular intervals, and therefore, the maximum angle of rotation of the light source holder 38 is 90°. By using such a structure in which the light source holder is rotatably driven together with the structure shown in FIG. 10 in which light sources are arranged on the circumferences of multiple circles, it is possible to provide more various light sources at positions outside the direct field of view and indirect field of view of the two-dimensional detector 6.

As has been described above, the lighting system of the biological image acquisition device is used as both an illumination light source for external image pickup and an excitation light source for fluorescence image pickup. In the case of external image pickup, light sources such as white LEDs are turned on to illuminate the biological specimen 4. At this time, a filter for eliminating wavelength components of illuminating light is not provided on the light-input side of the two-dimensional detector, and therefore, all the wavelength components contained in illuminating light enter the two-dimensional detector. If illumination light sources are arranged within the field of view of the two-dimensional detector, very strong direct light enters the two-dimensional detector so that problems such as blooming occur. However, in the above-described biological image acquisition device according to the present invention, light sources are arranged at positions outside both the direct field of view and indirect field of view of the two-dimensional detector, and therefore, direct light from the light sources does not enter the two-dimensional detector during external image pickup and thus problems such as blooming do not occur.

On the other hand, in the case of fluorescence image pickup, the specimen is irradiated with excitation light from which wavelength components that pass through the fluorescence-side filter 10 have been removed by an interference filter, and therefore, even when excitation light sources are arranged within the field of view of the two-dimensional detector, light emitted from the excitation light sources should be removed by the fluorescence-side filter 10 before entering the two-dimensional detector. Therefore, even when irradiation points are located at positions allowing them to be directly projected onto the two-dimensional detector, no problems should occur because the intensity of corresponding light is zero in theory. However, in reality, the interference filter cannot completely cut off light outside its pass band, and leak light of about $10^{-6}$ to $10^{-8}$ is produced. Therefore, if irradiation points are located at positions allowing them to be directly projected onto the two-dimensional detector, the images of the irradiation points are formed on the two-dimensional detector due to the leak light even when blooming does not occur. Particularly, in the case of the light source system shown in FIG. 8, an interference filter is used to remove light in a predetermined wavelength band from light emitted from a continuous light source such as a halogen lamp. Therefore, in this case, the amount of leak light is larger and direct light from light sources is more likely to be projected onto the two-dimensional detector as compared to a case where, as shown in FIG. 4a, light having a wavelength band within the skirt portion of the emission spectrum of an LD that is a single-wavelength light source is removed from light emitted from the LD using an interference filter.

The above description can be summarized as follows. The degree of adverse effect caused by direct projection of irradiation points onto the two-dimensional detector is largest when external images are picked up, and is second largest when fluorescence images are picked up using a continuous light source, and is relatively small when fluorescence images are picked up using a single-wavelength light source such as an LD. However, in any of these cases, it is only necessary to arrange light sources outside both the direct field of view and indirect field of view of the two-dimensional detector to avoid the problem that irradiation points are projected onto the two-dimensional detector. Therefore, the above-described technique according to the present invention is effective.

In a case where a plurality of reflection mirrors are arranged to increase the number of multi-directional images that can be simultaneously acquired, it is necessary to densely arrange reflection mirrors. In this case, it is difficult to arrange a plurality of excitation light sources so that each of them is located between adjacent reflection mirrors to emit light from the same direction as the observation direction in which the reflection mirror is arranged. However, even in such a case, as in the case of the embodiments described in this specification, the variety of excitation light sources can be increased by arranging light sources so that light is emitted from oblique directions with respect to the biological specimen 4.

It is to be noted that in each of the embodiments shown in FIGS. 1, 3, 5, 10, and 11, the two-dimensional detector and the lenses are arranged directly above the specimen for the sake of clarity, but the present invention is applicable also to the case where the device is tilted at an appropriate angle (e.g., 45° or 90°) in its entirety. In this case, the concept of "upper/lower side of the specimen" is eliminated. That is, an image of the specimen regarded as an upper-side image of the specimen in each of the above embodiments can be generally referred to as a two-dimensional detector-side image of the specimen. The word "two-dimensional detector-side image of the specimen" refers to an image which can be directly observed from a direction in which the two-dimensional detector is arranged. On the other hand, an image of the specimen regarded as a lower-side image of the specimen in each of the above embodiments can be generally referred to as an "image which can be directly observed from a direction other than the direction from which the "two-dimensional detector-side image of the specimen" can be directly observed". The word "lower-side image" used herein is not limited to an image observed from a 180° direction when the direction in which the two-dimensional detector is arranged is defined as a 0° direction. For example, in FIG. 5, images observed from the two directions of 144° and 212° are lower-side images, and therefore, images observed from the directions of 144° and 212° can be regarded as images on the opposite side from the two-dimensional detector.

When a direction within a range of 0° to 90° that is an angle between the direction in which the two-dimensional detector is arranged and the observation direction is defined as a "two-dimensional detector-side direction", a direction within a range of larger than 90° but 270° or less that is an angle between the direction in which the two-dimensional detector is arranged and the observation direction can be defined as "the other direction". The word "the other direction" can also be referred to as a direction within a range having an obtuse angle which is formed by the direction in which the two-dimensional detector is arranged and the observation direction. A backlight problem associated with multi-directional simultaneous observation, which is one of the problems to be solved by the present invention, occurs when the angle between the observation direction and the direction in which the two-dimensional detector is arranged is obtuse. However, even when the observation direction forms an obtuse angle with the direction in which the two-dimensional detector is arranged, such a problem as described above can be solved by arranging the illumination light sources outside the field of view of the two-dimensional detector.

Further, as described above, two or more two-dimensional detectors may be used. That is, an image on the opposite side from one of two or more two-dimensional detectors may be observed by the same two-dimensional detector as in the case of the embodiments shown in FIGS. 1 and 5, or may be observed by another two-dimensional detector as in the case of the embodiment shown in FIG. 9. In the case of the embodiment shown in FIG. 9, a specimen is simultaneously observed from four directions by two two-dimensional detectors. That is, the first two-dimensional detector is used to observe the specimen from the directions of 0° and 90°, and the second two-dimensional detector is used to observe the specimen from the directions of 180° and 270°. In general, two-dimensional detectors are expensive, and therefore, multi-directional observation is preferably performed by only one two-dimensional detector. However, for example, a device using two two-dimensional detectors for observation from four directions is cheaper than a device using four two-dimensional detectors for observation from four directions, and therefore, there is a merit in using two or more detectors. This is an example of a measurement system using two or more two-dimensional detectors, the number of which is less than the number of observation directions. The use of two or more two-dimensional detectors makes it possible to make the total area of a light-receiving surface of the detectors larger as compared to a case where only one detector is used. This is advantageous for detection of weak light such as luminescence measurement, while the device is slightly more expensive. As has been described above, the biological image acquisition device according to the present invention may have the option of using two or more two-dimensional detectors for multi-directional image pickup.

When the biological image acquisition device shown in FIG. 1 is tilted to the right by 90° while only the specimen support remains horizontal, the two-dimensional detector is located on the right-hand side of the specimen. In this case, the right-hand-side image of the specimen is regarded as a front-side (0°) image of the specimen observed from a direction in which the two-dimensional detector is arranged, and the left-hand-side image of the specimen is regarded as a back-side or opposite-side (180°) image of the specimen. Further, in this case, the two-dimensional detector is arranged in the right-hand side tangential direction of the specimen support.

Embodiment 3

An embodiment using concave mirrors as reflection mirrors will be described with reference to FIGS. 12 to 15.

Figure 12:
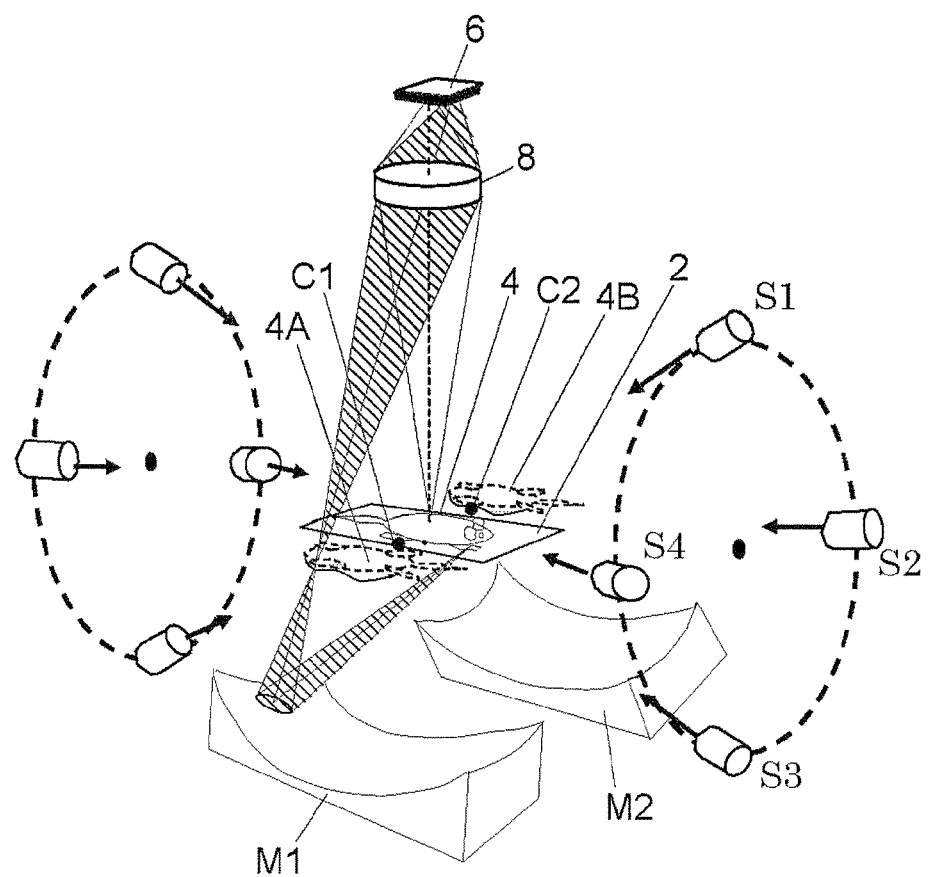
FIG. 12 is a perspective view showing the structure of a third embodiment of the biological image acquisition device according to the present invention using concave mirrors.

FIG. 12 is a perspective view of an embodiment that is the same as the first embodiment shown in FIGS. 1, 3A, and 3B except that the plane mirrors M1 and M2 are changed to concave mirrors. In this case, it is important that the center of curvature of the concave mirror M1 is set to a position C1 (represented by a black spot in FIG. 12) beside the abdomen of the specimen 4. The position C1 is at the same distance from the lens 8 as the specimen. Therefore, a diagonally bottom left-side image of the specimen as seen from the head-side of the specimen is formed at a position A4 adjacent to the specimen 4 by reflection from the concave mirror M1. Likewise, the center of curvature of the concave mirror M2 is set to a position C2 that is at the same distance from the lens 8 as the specimen. This makes it possible to form a diagonally bottom right-side image of the specimen at a position 4B adjacent to the specimen 4 by reflection from the concave mirror M2. These images formed adjacent to the specimen 4 are substantially the same as the specimen 4 in size but are inverted in the head-to-tail direction. The three images of the specimen 4, that is, the real image of the specimen 4 and the images 4A and 4B are at the same distance from the lens 8, and are therefore simultaneously focused by the lens 8 onto the CCD 6.

On the other hand, in a case where such plane mirrors as shown in FIGS. 3A and 3B are used, the back-side images of the specimen are formed at positions farther from a camera lens than the specimen, and therefore, three images are not at the same distance from the camera lens. This causes two drawbacks: one is that not all the three images are correctly focused; and the other is that the images formed at farther positions are smaller than the specimen. These two drawbacks can be overcome by replacing the plane mirrors with concave mirrors. This is very advantageous because when all the three images are at the same distance from the lens 8, correct focus can be obtained even when the lens 8 is bright at full aperture, and therefore, a lens having a small F number can be used to receive weak light emitted from the specimen. It is to be noted that the auxiliary imaging lens 12 disclosed in the first and second embodiments also has the function of shifting the focal position of an image formed at a farther position, but does not have the function of directly adjusting the size of an image formed at a farther position to the real size of the specimen. Further, it is additionally stated that such a system using an auxiliary lens has a drawback that it is difficult to use a main image forming lens at a low F number due to the limitation of the size of the auxiliary lens, and therefore, as described above with reference to the third embodiment, the use of concave mirrors is remarkably effective.

Light source units S1 to S4 used in the third embodiment will be described as follows. The light source units S1 to S4 are the same as those used in the above embodiments. However, the positioning of the light source units is important, because there is a case where the light sources are projected onto the CCD 6 depending on their positions.

Figure 13:
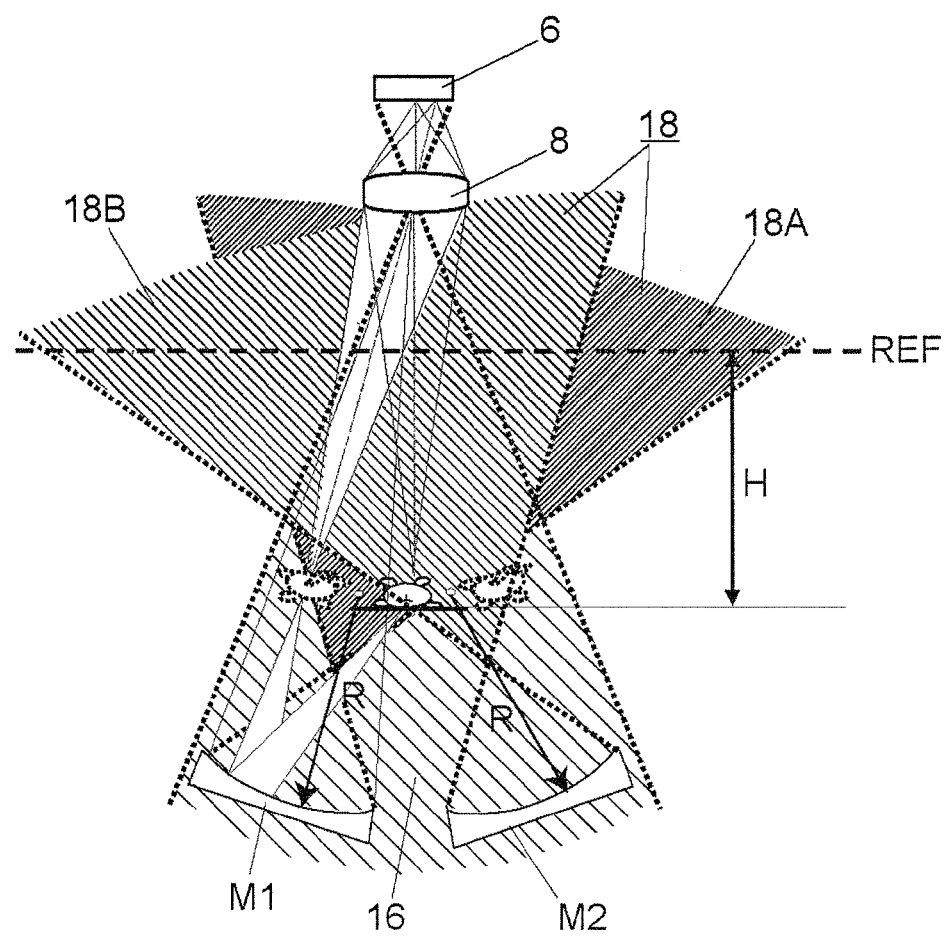
FIG. 13 is an explanatory diagram showing the direct and indirect field of view of a two-dimensional detector in a sectional plane when concave mirrors are used.

FIG. 13 is a sectional view showing the direct field of view and indirect field of view of the two-dimensional detector when concave mirrors are used as reflection mirrors. As in the case of the embodiment shown in FIG. 3B, the area 16 shown in FIG. 13 represents a direct field of view of the two-dimensional detector. When the reflection mirrors are not present, the light sources are not projected onto the two-dimensional detector as long as they are outside the direct field of view of the two-dimensional detector. The area 18 (including both an area 18A and an area 18B) represents an indirect field of view of the two-dimensional detector formed by the concave reflection mirrors, which is projected onto the two-dimensional detector through the concave reflection mirrors. More specifically, the area 18A represents an indirect field of view of the two-dimensional detector, which is projected onto the two-dimensional detector through the reflection mirror M1, and the area 18B represents an indirect field of view of the two-dimensional detector, which is projected onto the two-dimensional detector through the reflection mirror M2.

As shown in FIG. 13, the indirect field of view of the two-dimensional detector formed by the concave reflection mirrors within a sectional view can be relatively easily estimated, but the problem is the estimation of the indirect field of view in an area not included in the sectional view. In the case of using plane mirrors, as shown in FIG. 3A, projection of the light source units S1, S2, S3, and S4 onto the two-dimensional detector can be prevented by arranging them in a sectional plane which is perpendicular to the body axis of the specimen and whose center is located on an extension of the body axis of the specimen. However, in the case of using concave mirrors, estimation of three-dimensional field of view of the two-dimensional detector is slightly difficult.

Figure 14:
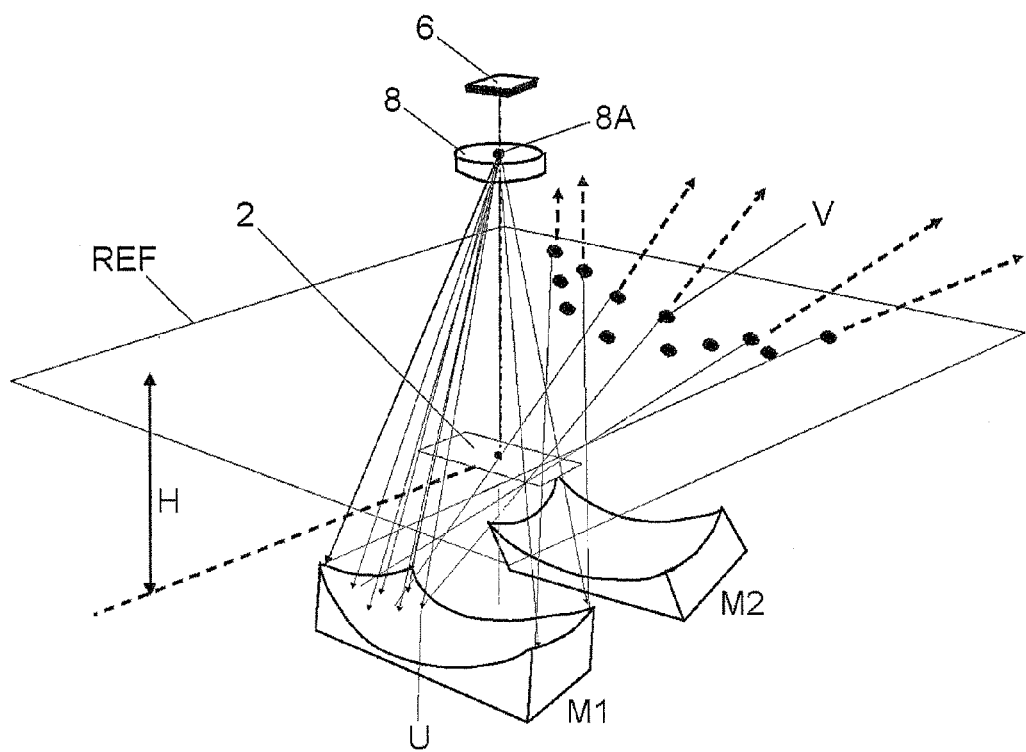
FIG. 14 is a diagram for explaining a method for calculating three-dimensional indirect field of view of a two-dimensional detector when concave mirrors are used.
Figure 15:
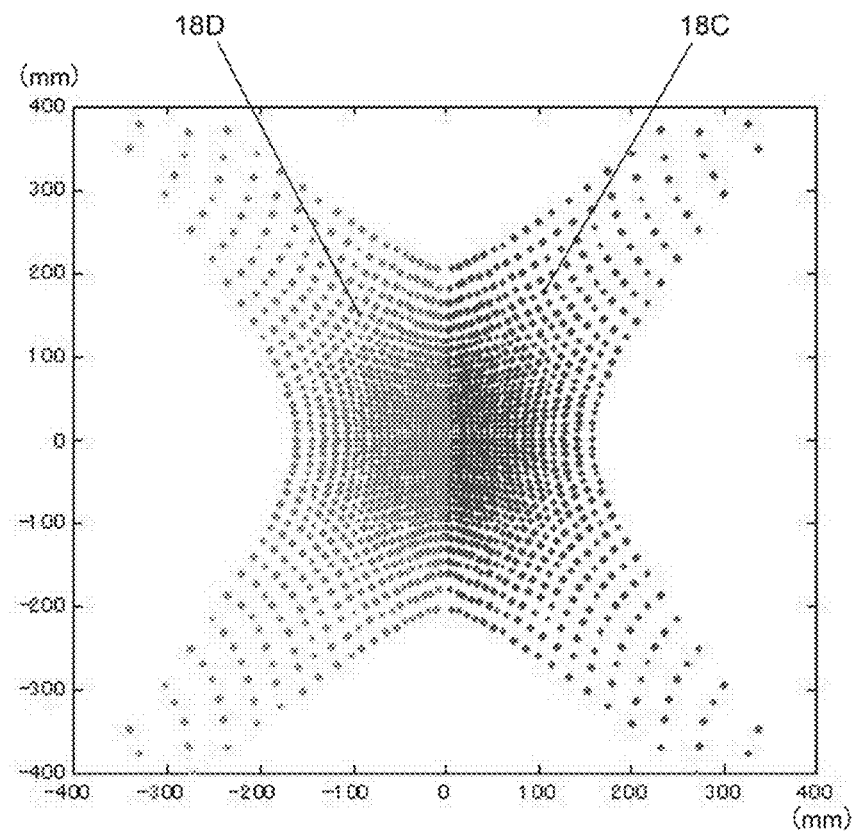
FIG. 15 is a distribution map of light beams impinging on a reference surface after reflection from a concave mirror M1 or M2.

A method for determining a three-dimensional indirect field of view by calculation will be described with reference to FIG. 14. In this calculation, a plurality of light beams are projected from a center 8A (i.e., a so-called principal point) of the lens 8 toward the concave mirror M1. Here, one of the light beams is defined as, for example, 8A-U. A point U is a point on the concave mirror M1. The light beams including the light beam 8A-U are reflected by the concave mirror M1 and then travel obliquely upward. When a virtual reference surface REF (a horizontal surface at a height of H from the specimen) is created, reflected light beams (one of which is a light beam U-V) impinge on the reference surface REF. Therefore, a distribution map of points (one of which is a point V), at which the reflected light beams impinge on the reference surface RFE, can be obtained. Likewise, a distribution map of light beams reflected by the reflection mirror M2 can also be obtained. FIG. 15 is a distribution map obtained by this calculation method. A distribution map 18C on the right-hand side of FIG. 15 is a distribution map of light beams impinging on the reference surface REF after reflection by the reflection mirror M1 and a distribution amp 18D on the left-hand side of FIG. 15 is a distribution map of light beams impinging on the reference surface REF after reflection by the reflection mirror M2. As can be seen from FIG. 15, projection of the light source units S1, S2, S3, and S4 onto the two-dimensional detector can be prevented by arranging them outside the range where the reflected light beams are distributed. The direct field of view of the two-dimensional detector can be of course easily determined, and therefore, even when concave mirrors are used as reflection mirrors, the indirect field of view of the two-dimensional detector can be determined so that all the light sources S1, S2, S3, and S4 can be arranged outside both the direct field of view and indirect field of view of the two-dimensional detector.

In reality, as can be seen from FIG. 15, the corners of the indirect field of view of the two-dimensional detector diagonally extend due to reflection from the corners of the reflection mirrors, and therefore, the light source units need to be arranged outside the diagonally-extended portions of the indirect field of view of the two-dimensional detector.

In the case of the above-described embodiment, two concave mirrors are provided, but different types of optical elements such as concave mirrors and plane mirrors may be used in combination. Also in this case, the indirect field of view of the two-dimensional detector can be determined by calculating the distribution of reflected light beams impinging on a reference surface at the time when a plurality of light beams are projected from the principal point of the lens toward each of the optical elements. Therefore, even in the case of a multi-directional simultaneous observation device using different types of optical elements, such as plane mirrors and concave mirrors, in combination, projection of light sources onto a two-dimensional detector can be prevented by arranging the light sources outside both the direct field of view and indirect field of view of the two-dimensional detector and therefore clear multi-directional images can be acquired.

The invention claimed is:
1. A biological image acquisition device comprising:
a specimen support for supporting a biological specimen placed thereon;

a two-dimensional detector;
an image pickup optical system for leading, to the two-dimensional detector, light traveling in a direction toward the two-dimensional detector from the specimen placed on the specimen support and light traveling in another direction from the specimen, and for forming images of these lights on the two-dimensional detector, the image pickup optical system comprising a reflection mirror which leads the light traveling in the other direction than the direction toward the two-dimensional detector directly to the two-dimensional detector from the reflection mirror;
a light source system comprising a light source arranged outside a field of view of the two-dimensional detector, the light source irradiating the specimen placed on the specimen support with light and irradiating at least a part of the reflection mirror with direct light, and the field of view comprising indirect field of view of the two-dimensional detector through the reflection mirror and direct field of view of the two-dimensional detector; and
an image display device for displaying images picked up by the two-dimensional detector,
wherein no light source is arranged within a field of view of the two-dimensional detector.

2. The biological image acquisition device according to claim 1,
wherein the number of reflections of "light to be measured" is less than or at most the same as the number of reflections of "interfering light", the "light to be measured" being the light emitted from the light source and then finally entering the two-dimensional detector after reflection from the specimen, and the interfering light being the light emitted from the light source and then entering the two-dimensional detector directly or after reflection from objects, including walls, other than the specimen.

3. The biological image acquisition device according to claim 1,
wherein the number of the two-dimensional detector is only one.

4. The biological image acquisition device according to claim 1,
wherein the number of the two-dimensional detectors is two or more, the two-dimensional detectors being arranged at such positions that they directly receive lights traveling in directions different from each other front the specimen placed on the specimen support, and
wherein the image pickup optical system is provided per each of the two-dimensional detectors.

5. The biological image acquisition device according to claim 1,
wherein the light source system comprises a light source holder holding a plurality of light sources in a plane perpendicular to a body axis of the biological specimen placed on the specimen support.

6. The biological image acquisition device according to claim 5,
wherein the light source holder holds the light sources on a circumference of a circle whose center is located on an extension of a body axis of the specimen placed on the specimen support.

7. The biological image acquisition device according to claim 6,
wherein the circumference: comprises two or more concentric circumferences different in radius.

8. The biological image acquisition device according, to claim 6,
wherein the light source system further comprises a support system which supports the light source holder so that the light source holder is capable of rotating around an axis passing through the center of the circumference and a driving system which rotates the light source holder.

9. The biological image acquisition device according to claim 1,
wherein the light source is a light source for illuminating the specimen to acquire external images of the specimen.

10. The biological image acquisition device according to claim 1,
wherein the light source is an excitation light source which emits excitation light for exciting the specimen to generate fluorescence to pick up fluorescence images of the specimen, and
wherein the image pickup optical system comprises a filter arranged between the specimen and the two-dimensional detector, the filter transmitting only light within a wavelength band of a fluorescence component when fluorescence images are picked up.

11. The biological image acquisition device according to claim 1,
wherein the light source comprises two or more types of light sources including a light source for illuminating the specimen to acquire external images of the specimen and/or an excitation light source which emits excitation light for exciting the specimen to generate fluorescence to pick up fluorescence images of the specimen, and
wherein the two or more types of light sources are turned on or off independently of each other.

12. The biological image acquisition device according to claim 1,
wherein the light source comprises two or more types of light sources including excitation light sources each of which emits excitation light for exciting the specimen to generate fluorescence to pick up fluorescence images of the specimen, and
wherein each of the light sources has a structure in which an optical filter is attached to a laser diode or a light-emitting diode.

13. The biological image acquisition device according to claim 1,
wherein the reflection mirror includes a plane reflection mirror.

14. The biological image acquisition device according to claim 1,
wherein the image pickup optical system comprises an auxiliary imaging lens that compensates for a difference in optical path length between lights of two or more images formed on the two-dimensional detector.

15. The biological image acquisition device according to claim 1,
wherein the reflection mirror includes a concave reflection mirror.

16. The biological image acquisition device according to claim 15,
wherein a center of curvature of the concave reflection mirror is set so as to be located at a position lateral to the specimen so that a distance between an imaging lens of a camera and the center of curvature of the concave reflection mirror is the same as that between the imaging lens of the camera and the specimen.

17. The biological image acquisition device according to claim 1,
- wherein the light source system comprises a white light source, a wavelength selection filter that selectively transmits only part of light emitted from the white light source and having a predetermined wavelength band, and an optical fiber for leading light passing through the wavelength selection filter to the light source, and
- wherein a wavelength band of light emitted from the light source is selected by switching a pass band of the wavelength selection filter.

* * * * *